United States Patent
Ono et al.

(10) Patent No.: US 9,278,989 B2
(45) Date of Patent: Mar. 8, 2016

(54) SUGAR-DERIVED GELATOR

(71) Applicants: KYUSHU UNIVERSITY, Fukuoka-shi, Fukuoka (JP); INSTITUTE OF SYSTEMS, INFORMATION TECHNOLOGIES AND NANOTECHNOLOGIES, Fukuoka-shi, Fukuoka (JP); NISSAN CHEMICAL INDUSTRIES, LTD., Tokyo (JP)

(72) Inventors: Fumiyasu Ono, Fukuoka (JP); Seiji Shinkai, Fukuoka (JP); Osamu Hirata, Funabashi (JP)

(73) Assignees: KYUSHU UNIVERSITY, Fukuoka-shi (JP); INSTITUTE OF SYSTEMS, INFORMATION TECHNOLOGIES AND NANOTECHNOLOGIES, Fukuoka-shi (JP); NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/383,654

(22) PCT Filed: Mar. 8, 2013

(86) PCT No.: PCT/JP2013/056493
§ 371 (c)(1),
(2) Date: Sep. 8, 2014

(87) PCT Pub. No.: WO2013/133419
PCT Pub. Date: Sep. 12, 2013

(65) Prior Publication Data
US 2015/0025157 A1    Jan. 22, 2015

(30) Foreign Application Priority Data

Mar. 8, 2012    (JP) ................. 2012-052272

(51) Int. Cl.
| | |
|---|---|
| *C07H 15/04* | (2006.01) |
| *A23L 1/05* | (2006.01) |
| *A61K 8/60* | (2006.01) |
| *C07H 9/04* | (2006.01) |
| *A61Q 19/00* | (2006.01) |
| *A61K 8/04* | (2006.01) |
| *A61K 47/26* | (2006.01) |
| *H01B 1/12* | (2006.01) |
| *H01M 10/052* | (2010.01) |

(Continued)

(52) U.S. Cl.
CPC . *C07H 15/04* (2013.01); *A23L 1/05* (2013.01); *A61K 8/042* (2013.01); *A61K 8/60* (2013.01); *A61K 47/26* (2013.01); *A61Q 19/00* (2013.01); *C07H 9/04* (2013.01); *C09K 3/00* (2013.01); *H01B 1/12* (2013.01); *H01M 10/052* (2013.01); *H01M 10/0565* (2013.01); *A23V 2002/00* (2013.01); *A61K 2800/10* (2013.01); *A61K 2800/48* (2013.01); *H01M 2300/0085* (2013.01)

(58) Field of Classification Search
CPC .................................. C07H 15/04; A23L 1/05
See application file for complete search history.

(56) References Cited

U.S. PATENT DOCUMENTS

2011/0136748 A1    6/2011    Vachy

FOREIGN PATENT DOCUMENTS

| JP | H01-139519 A | 6/1989 |
|---|---|---|
| JP | H0363224 A | 3/1991 |

(Continued)

OTHER PUBLICATIONS

Shinkai S. et al. "Sugar-Integrated Gelators of Organic Solvents". vol. 7, No. 20, 4328-4334, 2001, Chem. Eur. J.

(Continued)

*Primary Examiner* — Paul V Ward
(74) *Attorney, Agent, or Firm* — Oliff PLC

(57) ABSTRACT

There is provided a novel gelator containing a sugar derivative. A gelator including a compound of Formula (1) or Formula (2):

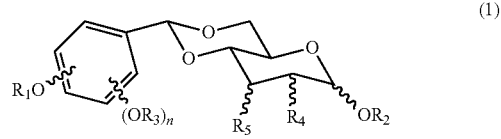

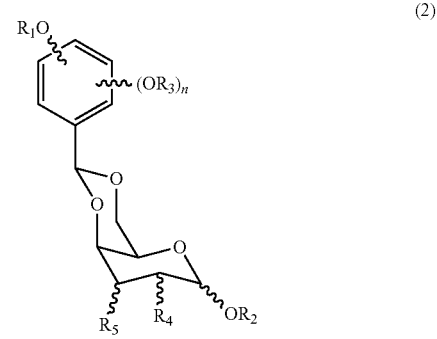

wherein each of $R_1$ and $R_3$ is independently a linear or branched alkyl group having a carbon atom number of 1 to 20, a cyclic $C_{3-20}$ alkyl group, or a linear or branched alkenyl group having a carbon atom number of 2 to 20, n is 0 or an integer of 1 to 4, $R_2$ is a hydrogen atom, a linear or branched alkyl group having a carbon atom number of 1 to 10, or an aryl group optionally having a substituent, and $R_4$ and $R_5$ are each a hydroxy group.

20 Claims, 6 Drawing Sheets

(51) Int. Cl.
      H01M 10/0565      (2010.01)
      C09K 3/00         (2006.01)

(56)            References Cited

FOREIGN PATENT DOCUMENTS

| JP | H03218390 A   | 9/1991  |
| JP | H10265761 A   | 10/1998 |
| JP | H11323309 A   | 11/1999 |
| JP | 2000256303 A  | 9/2000  |
| JP | 2004359643 A  | 12/2004 |
| WO | 2007/107285 A1| 9/2007  |

OTHER PUBLICATIONS

Abreu, Marlon et al., "Tuning methyl 4,6-O-benzylidene a-D-glucopyranosides' gelation ability by minor group modifications". vol. 353, 69-78, 2012.

Jun. 11, 2013 Written Opinion issued in International Application No. PCT/JP2013/056493.

Jul. 10, 2015 Search Report issued in European Application No. 13757549.4.

Lu et al., "New Synthetic Trisaccharide Inhibitors for N-Acetylglucosaminyltransferase-V," Bioorganic & Medicinal Chemistry, vol. 4, No. 11, pp. 2011-2022, 1996.

Wang et al., "Unique Reactivity of the Mukaiyama Glycosidation Catalyst (SnCl3ClO4) Toward B-Mannopyranosides," Chemistry—An Asian Journal, vol. 3, No. 2, pp. 319-326, 2008.

Geng et al., "Organocatalysis for the Acid-Free O-Arylidenation of Carbohydrates," European Journal of Organic Chemistry, vol. 2013, No. 31, pp. 7035-7040, 2013.

Selke et al., "Asymmetric Hydrogenation—Influence of the Structure of Carbohydrate Derived Catalysts on the Relative Enantioselectivity Q(H/Me) Regarding Acid and Ester Substrates and its Inversion—Selectivity Increase in Water by Amphiphiles," Tetrahedron, Elsevier Science Publishers, vol. 52, No. 48, pp. 15079-15102, 1996.

Khan et al., "Synthesis of Some Oligosaccharides Containing the O-(2-Acetamido-2-Deoxy-B-D-Glucopyranosyl)-(1~2)-O-a-D-Mannopyranosyl Unit. Potential Substrates for UDP-GlcNAc:a-D-mannopyranosyl-(1~6)-N-Acetyl-B-D-Glucosaminyltransferase (GnT-V)," Carbohydrate Research, Elsevier Science Publishers B.V., vol. 193, pp. 125-139, 1989.

Aspinall et al., "Structures of the glycopeptidolipid antigens of serovars 25 and 26 of the *Mycobacterium avium* serocomplex, synthesis of allyl glycosides of the outer disaccharide units and serology of the derived neoglycoproteins," Carbohydrate Research, Elsevier Science Publishers B.V., vol. 237, No. 1, pp. 57-77, 1992.

Amer et al., "Synthesis of O-Methylated Disaccharides Related to Excretory/Secretory Antigens of Toxocara Larvae," Journal of Carbohydrate Chemistry, vol. 20, No. 7&8, pp. 719-731, 2001.

Collins et al., "The Photochemistry of Carbohydrate Derivatives. Part IV. Photochemical Rearrangement of 4,6-O-o-Nitrobenzylideneglycopyranosides," Journal of the Chemical Society, Perkin Transactions 1, No. 17, pp. 1700-1706, 1975.

Yamamoto, "Preparation of p-Nitrophenyl 2-O-Acetyl-B-D-glucopyranoside and N-Acetyl-B-D-glucosaminidase Activity toward It. (Essential Requirement of 2-Acetamide Group of Substrate for N-Acetyl-B-D-glucosaminidase Hydrolysis)," Bulletin of the Chemical Society of Japan, vol. 46, No. 1, pp. 290-291, 1973.

Matta et al., "Synthesis of p-Nitrophenyl 6-O-(2-Acetamido-2-Deoxy-B-D-Glucopyranosyl)-B-D-Galactopyranoside and p-Nitrophenyl O-B-D-Galactopyransosyl-(1-3)-O-(2-Acetamido-2-Deoxy-B-D-Glycopyranosyl)-(1-6)-B-D-Galactopyranoside," Carbohydrate Research, vol. 53, No. 2, pp. 209-216, 1977.

Gronwald et al., "Sugar-Integrated Gelators of Organic Solvents," European Journal, vol. 7, No. 20, pp. 4328-4334, 2001.

Oct. 20, 2015 Extended European Search Report issued in European Application No. 13757549.4.

Dallacker et al.. "Synthesis and Reactions of 1,3-Benzodioxoledicarboxaldehydes A Contribution to the Structure Elucidation of Nepenthone-A," Zeitschrift fur Naturforschung B, pp. 1273-1280, Jan. 10, 1986.

| GELATOR | A | M1 | M3 |
|---|---|---|---|
| PHOTOGRAPH |  |  |  |
| SYNERESIS AMOUNT | LARGE | SMALL | TRACE |

* NUMERICAL VALUE IN DRAWING: wt% (GELATOR CONCENTRATION)

| GELATOR | M2 | M6 |
|---|---|---|
| PHOTOGRAPH OF GEL (TOLUENE GEL) |  (0.5wt%) |  (2wt%) |
| AFM IMAGE MAGNIFICATION: 10,000 TIMES |  |  |

| GEL | TOLUENE GEL: 0.5wt% | AQUEOUS GEL: 0.1wt% |
|---|---|---|
| PHOTOGRAPH OF GEL |  |  |
| XEROGEL SEM IMAGE TOLUENE GEL: MAGNIFICATION 10,000 TIMES AQUEOUS GEL: MAGNIFICATION 5,000 TIMES |  |  |

| GELATOR | M2 | G3 |
|---|---|---|
| PHOTOGRAPH OF GEL (AQUEOUS GEL) |  |  |
| XEROGEL SEM IMAGE<br><br>M2: MAGNIFICATION 5,000 TIMES<br>G3: MAGNIFICATION 25,000 TIMES |  |  |

SUGAR-DERIVED GELATOR

TECHNICAL FIELD

The present invention relates to a novel gelator containing a sugar derivative.

BACKGROUND ART

A structure that has a three-dimensional network structure formed by a substance having the ability to form a gel (hereinafter called a gelator) and contains a fluid in the network structure is called a gel. In general, a gel containing water as the fluid is called a hydrogel, and another gel containing an organic liquid (such as organic solvents and oils) except water is called an organogel or an oil gel. The oil gel (organogel) is used in the fields of cosmetics, pharmaceutical products, agrochemicals, foods, adhesives, paints, resins, and other products to control the flowabilities of cosmetics and paints. The oil gel (organogel) is also widely used in the field of environmental preservation, for example, to form a gel as a solid from oil waste, thus preventing water pollution.

Gelators have been studied mainly on polymer compounds, but in recent years, low-molecular weight compounds, to which various functions can be easily introduced as compared with the polymer compounds, have been being studied. As described above, the oil gels (organogels) have been used in a wide variety of fields and are expected to be used in wider fields in future. On this account, as the application fields of the oil gels expand, gelators of low-molecular weight compounds (hereinafter also called low-molecular weight gelators) are required to have ability to form a gel from a wide variety of organic solvents. To address these requirements, a urea compound has been disclosed as a low-molecular weight gelator capable of forming a gel having excellent stability from various organic solvents by adding a small amount of the compound (for example, Patent Documents 1 and 2). It is also disclosed that an α-aminolactam derivative has the ability to form gels from squalane, a liquid paraffin, and other substances (for example, Patent Document 3).

Sugar derivatives derived from various monosaccharides have a structure readily forming strong hydrogen bonds to each other, and it has been disclosed that the sugar derivatives form gels from various organic solvents (Non-Patent Document 1).

PRIOR ART DOCUMENTS

Patent Documents

Patent Document 1: Japanese Patent Application Publication No. 2000-256303 (JP 2000-256303 A)
Patent Document 2: Japanese Patent Application Publication No. 2004-359643 (JP 2004-359643 A)
Patent Document 3: Japanese Patent Application Publication No. 10-265761 (JP 10-265761 A)

Non-Patent Document

Non-Patent Document 1: S. Shinkai et al., Chem. Eur. J., 2001, 7, No. 20, 4328-4334

SUMMARY OF THE INVENTION

Problem to be Solved by the Invention

Oil gelators of low-molecular weight compounds for non-aqueous mediums such as organic solvents have been developed, but have disadvantages such that mediums for forming a gel are limited. On this account, in order to develop a novel oil gel having new applications and functions, a new low-molecular weight oil gelator capable of forming gels from various mediums have been sought. Gelators of sugar derivatives can form gels from various solvents by changing the type of the sugar. However, it is quite difficult to form gels from a wide variety of solvents by using a single sugar derivative. A gel obtained by using the sugar derivative described in Non-Patent Document 1 has no storage stability.

No gelator capable of forming a gel from both solvents of water and oil (hydrophilic organic solvents and hydrophobic organic solvents) has been developed as far as the inventors of the present invention know, and a gelator exerting such a gelation performance has been demanded until now. In particular, a gelator capable of forming a gel from a mixed solvent of water and oil (a hydrophobic organic solvent) without using a surfactant or a similar agent is useful in base materials for cosmetics and pharmaceutical products, which require high biological safety, but such a revolutionary gelator has not been developed.

In view of the above, it is an object of the present invention to provide a novel gelator having a structure that has not been developed. In particular, the inventors of the present invention have found a glucose gelator that can form a gel not only from water or oil (hydrophilic organic solvents and hydrophobic organic solvents) alone but also from a mixed solvent of water and oil (hydrophilic organic solvents and hydrophobic organic solvents), especially, from a mixed solvent of water and oil (hydrophobic organic solvents), and have accomplished the present invention.

Means for Solving the Problem

As a result of intensive studies for solving the disadvantages, the inventors of the present invention have found that by converting substituents on a sugar derivative and using the resultant product as a gelator for water, organic solvents, and other liquids, the gelator surprisingly can form a gel from both an organic solvent and water without changing the type of the sugar used for the sugar derivative and that control of the type of substituents allows a change in the type of a solvent that is to form a gel, and have accomplished the present invention.

Specifically, as a first aspect, the present invention relates to a gelator comprising a compound of Formula (1) or Formula (2):

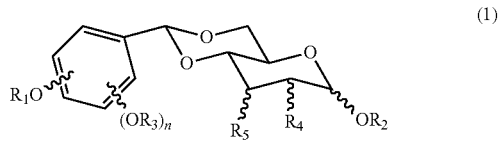

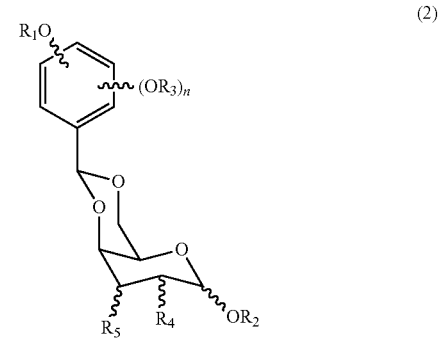

(where
each of $R_1$ and $R_3$ is independently a linear or branched alkyl group having a carbon atom number of 1 to 20, a cyclic $C_{3-20}$ alkyl group, or a linear or branched alkenyl group having a carbon atom number of 2 to 20; n is 0 or an integer of 1 to 4;

$R_2$ is a hydrogen atom, a linear or branched alkyl group having a carbon atom number of 1 to 10, or an aryl group optionally having a substituent; and $R_4$ and $R_5$ are each a hydroxy group).

As a second aspect, the present invention relates to the gelator according to the first aspect, in which the compound of Formula (1) is a compound of Formula (3):

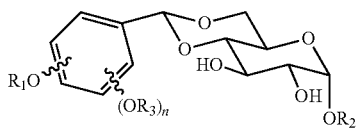
(3)

[where $R_1$, $R_2$, $R_3$, and n are the same as the respective definitions described in Formula (1)].

As a third aspect, the present invention relates to the gelator according to the first aspect, in which the compound of Formula (1) is a compound of Formula (4):

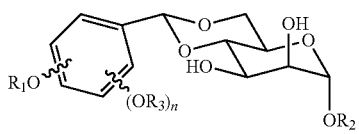
(4)

[where $R_1$, $R_2$, $R_3$, and n are the same as the respective definitions described in Formula (1)].

As a fourth aspect, the present invention relates to a gel comprising the gelator as described in any one of the first aspect to the third aspect and a hydrophobic organic solvent, a hydrophilic organic solvent, water, a hydrophilic organic solution, a hydrophobic organic solution, or an aqueous solution.

As a fifth aspect, the present invention relates to the gel according to the fourth aspect, in which the hydrophobic organic solvent is at least one selected from the group consisting of plant oils, esters, silicone oils, and hydrocarbons.

As a sixth aspect, the present invention relates to the gel according to the fourth aspect, in which the hydrophilic organic solvent is at least one selected from the group consisting of methanol, ethanol, 2-propanol, i-butanol, pentanol, hexanol, 1-octanol, isooctanol, acetone, cyclohexanone, acetonitrile, dioxane, glycerol, propylene glycol, ethylene glycol, and dimethyl sulfoxide.

As a seventh aspect, the present invention relates to the gel according to the fourth aspect, in which the hydrophilic organic solution is a mixed solvent of the hydrophilic organic solvent as described in the sixth aspect and water.

As an eighth aspect, the present invention relates to the gel according to the fifth aspect, in which the hydrophobic organic solution is a mixed solvent of the hydrophobic organic solvent as described in the fifth aspect and water.

As a ninth aspect, the present invention relates to the gel according to the fourth aspect, in which the aqueous solution is an aqueous solution containing an organic acid, an inorganic acid, at least one inorganic salt selected from the group consisting of inorganic carbonates, inorganic sulfates, inorganic phosphates, and inorganic hydrogen phosphates, or at least one organic salt selected from the group consisting of acetates, lactates, citrates, organic amine hydrochlorides, and organic amine acetates.

As a tenth aspect, the present invention relates to the gel according to the ninth aspect, in which the organic acid is at least one selected from the group consisting of acetic acid, citric acid, succinic acid, lactic acid, malic acid, maleic acid, fumaric acid, and trifluoroacetic acid, the inorganic acid is at least one selected from the group consisting of hydrochloric acid, phosphoric acid, carbonic acid, sulfuric acid, nitric acid, and boric acid, the inorganic salt is at least one selected from the group consisting of calcium carbonate, sodium carbonate, potassium carbonate, sodium sulfate, potassium sulfate, magnesium sulfate, potassium phosphate, sodium phosphate, disodium hydrogen phosphate, and sodium dihydrogen phosphate, and the organic salt is at least one selected from the group consisting of sodium acetate, potassium acetate, sodium lactate, potassium lactate, sodium citrate, potassium citrate, ethylenediamine hydrochloride, ethylenediaminetetraacetate, and trishydroxymethylaminomethane hydrochloride.

As an eleventh aspect, the present invention relates to a base material for cosmetics or a base material for medical use, the base material comprising the gelator as described in any one of the first aspect to the third aspect.

As a twelfth aspect, the present invention relates to a base material for cosmetics or a base material for medical use, the base material comprising the gelator as described in any one of the first aspect to the third aspect and at least one polymer compound.

As a thirteenth aspect, the present invention relates to a gel electrolyte comprising the gelator as described in any one of the first aspect to the third aspect.

As a fourteenth aspect, the present invention relates to a cell culture base material comprising the gelator as described in any one of the first aspect to the third aspect.

As a fifteenth aspect, the present invention relates to a base material for preserving biomolecules, the base material comprising the gelator as described in any one of the first aspect to the third aspect.

As a sixteenth aspect, the present invention relates to a base material for external use, the base material comprising the gelator as described in any one of the first aspect to the third aspect.

As a seventeenth aspect, the present invention relates to a base material for biochemistry, the base material comprising the gelator as described in any one of the first aspect to the third aspect.

As an eighteenth aspect, the present invention relates to a base material for food, the base material comprising the gelator as described in any one of the first aspect to the third aspect.

As a nineteenth aspect, the present invention relates to a base material for dryland farming, the base material comprising the gelator as described in any one of the first aspect to the third aspect.

As a twentieth aspect, the present invention relates to a method for producing the compound of Formula (1) or Formula (2) as described in the first aspect, the method characterized by comprising reacting a compound of Formula [A]:

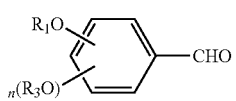
[A]

(where each of $R_1$ and $R_3$ is independently a linear or branched alkyl group having a carbon atom number of 1 to 20, a cyclic $C_{3-20}$ alkyl group, or a linear or branched alkenyl group having a carbon atom number of 2 to 20; and n is 0 or an integer of 1 to 4) with an acetalizing agent, and subsequently subjecting the obtained acetal derivative to annulation reaction with glucose, mannose, a derivative of glucose, or a derivative of mannose, thus producing the compound of Formula (1) or Formula (2), in which the reactions are carried out in a one-pot system in the presence of ethanol and p-toluenesulfonic acid.

Effects of the Invention

The gelator of the present invention can form a gel from an aqueous system, an organic solvent system, or both the systems. In addition, by changing the type of a substituent on a sugar derivative of the gelator of the present invention, the type of a solvent that is to form a gel can be changed. The gelator of the present invention has good storage stability.

The gelator of the present invention is produced from a monosaccharide such as glucose, mannose, and derivatives thereof as raw materials, and thus can form a gel having excellent biological safety.

In particular, the compound of Formula (3) (hereinafter called a glucose gelator) having a glucose moiety is produced from glucose, which is a common monosaccharide. This can reduce the material cost for producing the gelator to an extremely low level. In addition, the synthesis of the gelator achieves a high total yield throughout all processes and is unlikely to cause side reactions. Thus, the glucose gelator can be easily produced as compared with related art gelators, and the production cost can be extremely reduced. Furthermore, the glucose gelator has the ability to form gels from both water and oil (hydrophobic organic solvents) and can form a water/oil dispersion gel. The glucose gelator can also form a gel from alcoholic solvents. On this account, the glucose gelator is a highly versatile gelator that can be used at a low concentration to form a transparent gel from mediums having a wide variety of characteristics. In particular, the glucose gelator can form a highly transparent gel from water.

The compound of Formula (4) (hereinafter called a mannose gelator) having a mannose moiety can form a highly transparent gel from oil (hydrophilic organic solvents and hydrophobic organic solvents) and can yield a gel having excellent thixotropic properties. The mannose gelator can form a self-standing, transparent gel (having self-standing properties) and thus is useful for a base material for sticks.

The production method of the present invention can produce the above-mentioned gelator from derivatives of glucose and mannose in a one-pot system and can simply, inexpensively produce a compound to be the gelator. In addition, the method eliminates methanol and metal catalysts during the production and thus can produce a compound usable as the gelator particularly for base materials that are required to have high safety, such as base materials for cosmetics, base materials for medical use, and base materials for food.

BRIEF DESCRIPTION OF THE DRAWINGS

FIG. 9A is a view showing the gel immediately after the release; FIG. 9B is a view showing gels prepared by cutting the released gel with a cover glass (a thickness of 0.12 to 0.17 mm); and FIG. 9C is a view showing a stacked gel by joining the cut sections of the cut gel to each other.

MODES FOR CARRYING OUT THE INVENTION

[Gelator]

Figure 1:
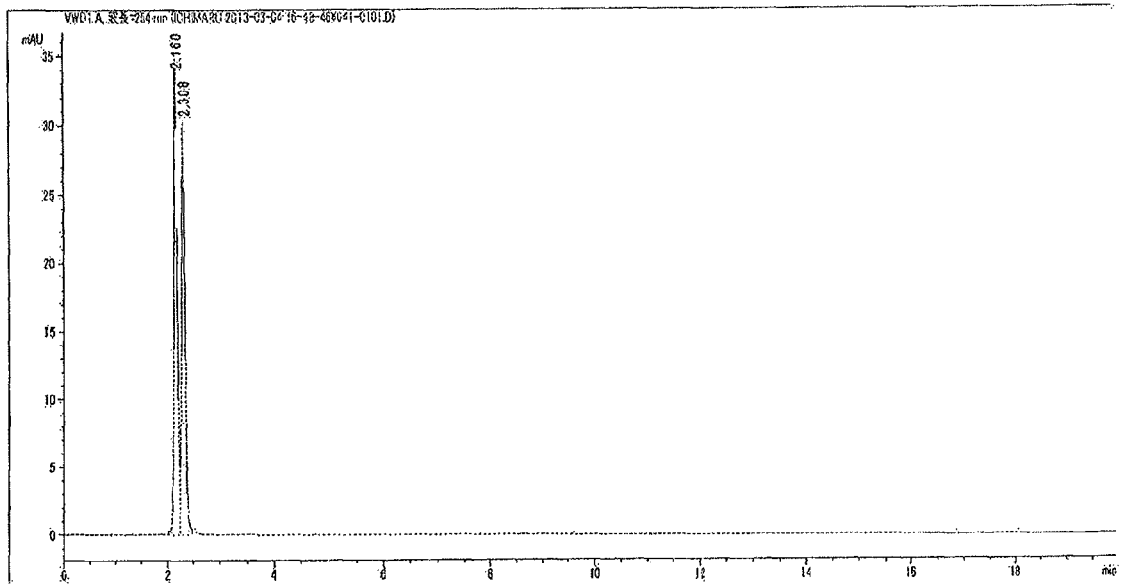
FIG. 1 is a view showing an HPLC chart of a purified compound [G3"] prepared in Examples.

The gelator of the present invention comprises a compound of Formula (1) or Formula (2).

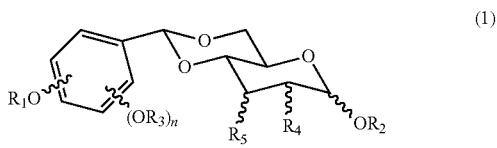

(1)

-continued

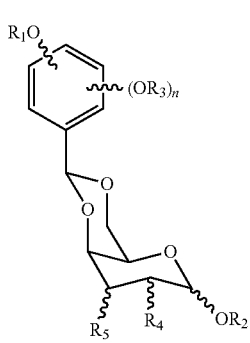

(2)

(In the formulae, each of $R_1$ and $R_3$ is independently a linear or branched alkyl group having a carbon atom number of 1 to 20, a cyclic $C_{3-20}$ alkyl group, or a linear or branched alkenyl group having a carbon atom number of 2 to 20; n is 0 or an integer of 1 to 4;

$R_2$ is a hydrogen atom, a linear or branched alkyl group having a carbon atom number of 1 to 10, or an aryl group optionally having a substituent; and $R_4$ and $R_5$ are each a hydroxy group)

Examples of the linear alkyl group having a carbon atom number of 1 to 20 include a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-eicosyl group.

Examples of the branched $C_{1-20}$ alkyl group include an isopropyl group, an isobutyl group, a sec-butyl group, a tert-butyl group, and a 2-ethylhexyl group.

Examples of the cyclic $C_{3-20}$ alkyl group include groups having a cyclopentyl ring structure and groups having a cyclohexyl ring structure.

Examples of the linear $C_{2-20}$ alkenyl group include a vinyl group, an allyl group, a butenyl group, a pentenyl group, a hexenyl group, a heptenyl group, an octenyl group, a nonenyl group, and a decenyl group.

Examples of the branched $C_{2-20}$ alkenyl group include a 2-methyl-2-propenyl group, an isopropenyl group, a 2-methyl-1-propenyl group, and a 2-methylallyl group.

Examples of the linear or branched alkyl group having a carbon atom number of 1 to 10 include groups having a carbon atom number of 1 to 10 among the groups exemplified as the linear $C_{1-20}$ alkyl group and as the branched $C_{1-20}$ alkyl group.

Examples of the aryl group include a phenyl group, a benzyl group, a 1-naphthyl group, a 2-naphthyl group, a 1-anthryl group, and a 1-phenanthryl group. The aryl group may have a substituent, and examples of the substituent include linear, branched, and cyclic alkyl groups optionally having an ester linkage, an amide linkage, or an ether linkage and halogen atoms.

From the viewpoint that the gelator of the present invention is used to form a good gel from a solvent, $R_2$ is preferably a hydrogen atom or a methyl group in Formula (1) or (2).

From the viewpoint that the gelator can form a highly transparent gel without syneresis when used for a hydrophobic organic solvent, $R_1$ is preferably a butyl group, a pentyl group, or a hexyl group.

From the viewpoint that the gelator can form a highly transparent gel without syneresis when used for a hydrophilic organic solvent, $R_1$ is preferably an octyl group, a decyl group, or a dodecyl group.

From the viewpoint that the gelator can form a highly uniform gel from water optionally containing a hydrophilic organic solvent, a hydrophobic organic solvent such as oils, or a mixture of both the solvents, $R_1$ is preferably a propyl group, a butyl group, or a pentyl group.

The compound of Formula (1) or (2) can be produced by a known method, for example, by reacting a benzaldehyde dimethyl acetal having the above-mentioned substituents on the benzene ring with a monosaccharide.

The monosaccharide may be any monosaccharide having a pyranose ring structure, and usable examples of the monosaccharide include allose, altrose, glucose, mannose, gulose, idose, galactose, and talose.

Among them, the monosaccharide is preferably glucose and mannose from the viewpoint that such monosaccharides are relatively inexpensive and should particularly provide biocompatibility.

Among the compounds of Formula (1) and (2), a compound of Formula (3) having a glucose moiety or a compound of Formula (4) having a mannose moiety is particularly preferred.

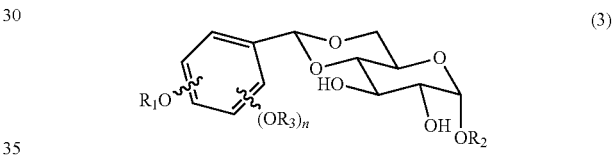

(3)

[In the formula, $R_1$, $R_2$, $R_3$, and n are the same as the respective definitions described in Formula (1)]

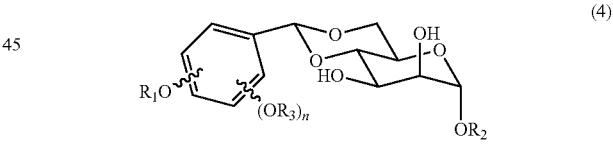

(4)

[In the formula, $R_1$, $R_2$, $R_3$, and n are the same as the respective definitions described in Formula (1)]

Among the compounds of Formula (3), a compound of Formula (5) is preferred, and a compound of Formula (7) is more preferred.

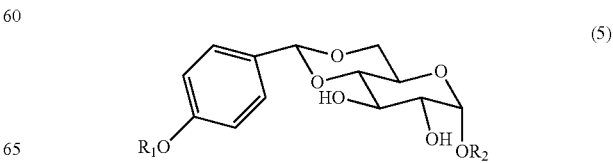

(5)

[In the formula, $R_1$ and $R_2$ are the same as the respective definitions described in Formula (1)]

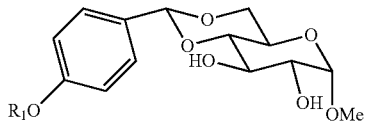

(7)

[In the formula, $R_1$ is the same as the definition described in Formula (1)]

Among the compounds of Formula (4), a compound of Formula (6) is preferred, and a compound of Formula (8) is more preferred.

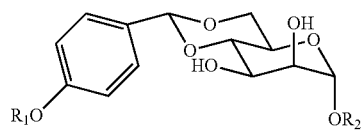

(7)

[In the formula, $R_1$ and $R_2$ are the same as the respective definitions described in Formula (1)]

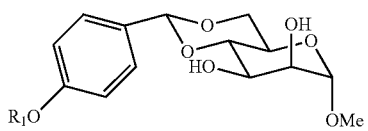

(8)

[In the formula, $R_1$ is the same as the definition described in Formula (1)]

As described above, the gel forming ability of the compound of Formula (3) (glucose gelator) is quite different from the gel forming ability of the compound of Formula (4) (mannose gelator). For example, the compounds can form gels from solvents, which varies with the compounds.

In particular, the compound of Formula (3) (glucose gelator) has the ability to form a gel from both water and oil (hydrophobic organic solvents), which is the greatest feature of the glucose gelator, and can form a water/oil dispersion gel from a mixed solvent of water and oil. In addition, the compound of Formula (3) can form a gel from an alcoholic solvent and forms a highly transparent gel from water.

The compound of Formula (4) (mannose gelator) can form a highly transparent gel from oil (hydrophilic organic solvents and hydrophobic organic solvents) and can yield a gel having excellent thixotropic properties. The compound of Formula (4) also can characteristically form a self-standing, transparent gel (having self-standing properties).

As described above, the glucose gelator and the mannose gelator have different gel forming abilities, and thus should be applied to a wide variety of fields suitable to the respective features.

[Gel]

A gel of the present invention can be produced by gelation of a solvent with the gelator. Specifically, the production method is exemplified by dissolving a predetermined amount of the gelator in a solvent with heating and then cooling the solution. Typically, for the dissolution with heating, the gelator is preferably, completely dissolved.

In the present application, the gelation means making a flowable liquid lose the flowability.

For the gelation of a solvent, the amount of the gelator of the present invention is not limited as long as the effects of the present invention are exerted, but is typically 20 to 0.001% by mass and preferably 2 to 0.05% by mass relative to the mass of a solvent to form a gel.

The solvent is not limited as long as the gelation is not suppressed, and preferred examples of the solvent specifically include hydrophobic organic solvents, hydrophilic organic solvents, water, mixed solvents of water and hydrophilic organic solvents (in the present specification, called hydrophilic organic solutions), mixed solvents of hydrophobic organic solvents and water (in the present specification, called hydrophobic organic solutions), and aqueous solutions in which an organic acid or an inorganic acid is dissolved in water or an inorganic salt or an organic salt is dissolved in water (in the present specification, called aqueous solutions).

Specific examples of the hydrophobic organic solvent include plant oils such as olive oil, coconut oil, castor oil, jojoba oil, and sunflower oil; esters such as cetyl octanoate, isopropyl myristate, and isopropyl palmitate; and hydrocarbons such as toluene, xylene, n-hexane, cyclohexane, octane, mineral oils, silicone oils, and hydrogenated polyisobutene.

Among them, the hydrophobic organic solvent is preferably olive oil, isopropyl myristate, toluene, cyclohexane, silicone oils such as linear silicones, cyclic silicones, alkyl-modified silicones, phenyl-modified silicones, dimethicone, and dimethiconol, and octane.

The silicone oil may be linear silicone (trade name: 2-1184), cyclic silicone (trade name: SH245), alkyl-modified silicone (trade name: SS-3408), phenyl-modified silicone (trade name: PH-1555), dimethicone (trade name: BY-11-0 series), and dimethiconol (trade name: CB-1556) available from Dow Corning Toray Silicone Co., Ltd., for example.

The hydrophilic organic solvent means an organic solvent that can be dissolved in water at any ratio and is exemplified by alcohols, acetone, cyclohexanone, acetonitrile, dioxane, glycerol, and dimethyl sulfoxide.

The alcohol is preferably water-soluble alcohols that can be freely dissolved in water and is more preferably exemplified by $C_{1-9}$ alcohols, polyhydric alcohols, higher alcohols, and glycerides.

Specific examples of the $C_{1-9}$ alcohol include methanol, ethanol, 2-propanol, i-butanol, pentanol, hexanol, 1-octanol, and isooctanol; specific examples of the polyhydric alcohol include ethylene glycol, propylene glycol, and polypropylene glycol; specific examples of the higher alcohol include octyldodecanol, stearyl alcohol, and oleyl alcohol; and specific examples of the glyceride include trioctanoin, capric/caprylic triglyceride, and glyceryl stearate.

Among them, the hydrophilic organic solvent is preferably methanol, ethanol, 2-propanol, i-butanol, pentanol, hexanol, 1-octanol, isooctanol, acetone, cyclohexanone, acetonitrile, dioxane, glycerol, propylene glycol, ethylene glycol, and dimethyl sulfoxide, and more preferably glycerol, propylene glycol, and ethylene glycol.

A plurality of the organic acids or the inorganic acids may be added. Preferred examples of the organic acid include acetic acid, citric acid, succinic acid, lactic acid, malic acid, maleic acid, fumaric acid, and trifluoroacetic acid. The organic acid is more preferably acetic acid, citric acid, succinic acid, lactic acid, and malic acid, and even more preferably acetic acid, citric acid, and lactic acid.

Preferred examples of the inorganic acid include hydrochloric acid, phosphoric acid, carbonic acid, sulfuric acid, nitric acid, and boric acid. The inorganic acid is more preferably hydrochloric acid, phosphoric acid, carbonic acid, and sulfuric acid, and even more preferably hydrochloric acid, phosphoric acid, and carbonic acid.

A plurality of the inorganic salts or the organic salts may be added, but one or two salts are preferably added. A solution obtaining a buffer capacity by adding two salts is also preferred.

Preferred examples of the inorganic salt include inorganic carbonates, inorganic sulfates, inorganic phosphates, and inorganic hydrogen phosphates. The inorganic salt is more preferably calcium carbonate, sodium carbonate, potassium carbonate, sodium sulfate, potassium sulfate, magnesium sulfate, potassium phosphate, sodium phosphate, disodium hydrogen phosphate, and sodium dihydrogen phosphate, and even more preferably calcium carbonate, magnesium sulfate, disodium hydrogen phosphate, and sodium dihydrogen phosphate.

Preferred examples of the organic salt include salts of organic acids with inorganic bases, such as inorganic acetates, inorganic lactates, and inorganic citrates, hydrochlorides of organic amines, and acetates of organic amines. The organic salt is more preferably sodium acetate, potassium acetate, sodium lactate, potassium lactate, sodium citrate, potassium citrate, ethylenediamine hydrochloride, ethylenediaminetetraacetate, and trishydroxymethylaminomethane hydrochloride.

The gelator of the present invention is used in an amount of 0.001 to 10% by mass, preferably 0.1 to 10% by mass, for example, 0.1 to 5% by mass relative to the hydrophobic organic solvent, the hydrophilic organic solvent, the water, the hydrophilic organic solution, the hydrophobic organic solution, or the aqueous solution as a medium.

The gelator of the present invention is added to the hydrophobic organic solvent, the hydrophilic organic solvent, the water, the hydrophilic organic solution, the hydrophobic organic solution, or the aqueous solution as a medium, and is dissolved by stirring with heating, as necessary, and then the solution is left at room temperature, thus yielding a gel. The strength of the gel can be adjusted by the concentration of the gelator.

The gel formed with the gelator of the present invention may contain various additives (including organic compounds such as surfactants, ultraviolet absorbers, moisturizers, antiseptics, antioxidants, aromatics, and physiologically active substances (medical components) and inorganic compounds such as titanium oxide, talc, mica, and water) depending on applications and purposes, as necessary, to an extent not impairing the gel forming ability of the gelator.

[Base Material for Cosmetics or Base Material for Medical Use]

A base material for cosmetics or a base material for medical use of the present invention includes the above-mentioned gelator.

The base material for cosmetics or the base material for medical use of the present invention can contain water, alcohols, polyhydric alcohols, hydrophilic organic solvents, hydrophobic organic solvents, and mixed solutions of them in addition to the gelator. Examples of the alcohol, the polyhydric alcohol, the hydrophilic organic solvent, and the hydrophobic organic solvent include the compounds exemplified as the alcohol, the polyhydric alcohol, the hydrophilic organic solvent, and the hydrophobic organic solvent.

The base material for cosmetics or the base material for medical use of the present invention can contain additives such as physiological active substances and functional substances that are commonly contained in base materials for cosmetics or base materials for medical use, as necessary.

Examples of such additives include oil base materials, moisturizers, texture improvers, surfactants, polymers, thickeners/gelators, solvents, propellants, antioxidants, reducing agents, oxidizing agents, preservatives, antimicrobial agents, antiseptics, chelating agents, pH adjusters, acids, alkalis, fine particles, inorganic salts, ultraviolet absorbers, whitening agents, vitamins and derivatives thereof, hair growth-promoting agents, blood circulation promoters, stimulants, hormones, anti-wrinkle agents, anti-aging agents, slimming agents, cooling agents, warming agents, wound healing promoters, abirritants, analgesics, cell activators, plant/animal/microbial extracts, antipruritics, cuticle peeling and dissolving agents, antiperspirants, algefacients, styptics, enzymes, nucleic acids, perfumes, coloring agents, colorants, dyes, pigments, antiphlogistics, anti-inflammatory agents, anti-asthmatic agents, agents for chronic obstructive pulmonary diseases, antiallergic agents, immunomodulators, anti-infective agents, and antifungal agents.

The base material for cosmetics or the base material for medical use of the present invention contains the gelator and at least one polymer compound.

Examples of the polymer compound include gelatin, sodium alginate, propylene glycol alginate, gum arabic, polyvinyl alcohol, polyacrylic acid, sodium polyacrylate, carboxymethylcellulose, gellan gum, xanthan gum, carrageenan polystyrene, polymethyl methacrylate, polyvinylpyrrolidone, polyethylene oxide, polylactic acid, polystyrene sulfonate, polyacrylonitrile, polyethylene, and polyethylene terephthalate.

[Gel Electrolyte]

A gel electrolyte of the present invention is obtained by gelation of an electrolytic solution (liquid electrolyte) including an organic solvent or water. The gelator and the electrolytic solution to be used are not limited and may be appropriately selected depending on an intended use.

For example, the electrolytic solution including an organic solvent is a solution of an electrolyte salt in at least one aprotic organic solvent.

Examples of the aprotic organic solvent include glyme, alkene carbonates, alkyl carbonates, cyclic ethers, amides, nitriles, ketones, and esters. Preferred examples of the aprotic organic solvent specifically include propylene carbonate, ethylene carbonate, diethyl carbonate, γ-butyrolactone, 1,2-dimethoxyethane, tetrahydrofuran, 2-methyltetrahydrofuran, dimethyl sulfoxide, 1,3-dioxolane, formamide, dimethylformamide, 1,4-dioxane, acetonitrile, nitromethane, ethyl monoglyme, phosphotriester, trimethoxymethane, dioxolane derivatives, sulfolane, 3-methyl-2-oxazolidinone, propylene carbonate derivatives, tetrahydrofuran derivatives, diethyl ether, and 1,3-propane sultone. These organic solvents can be used singly or in combination of two or more of them.

The electrolyte salt is composed of a cationic metal and a counter anion. Examples of the cationic metal include $Li^+$, $Na^+$, and $K^+$. Examples of the counter anion include $ClO_4^-$, $LiBF_4^-$, $PF_6^-$, $CF_3SO_3^-$, $CF_3CO_2$, $AsF_6^-$, $SbF_6^-$, $(CF_3SO_2)_2N^-$, $B_{10}Cl_{10}^{2-}$, $(1,2\text{-dimethoxyethane})_2ClO_4^-$, lower aliphatic carboxylates, $AlCl_4^-$, $Cl^-$, $Br^-$, $I^-$, chloroborane compounds, and tetraphenylboric acid. Among them, a preferred electrolyte salt is exemplified by lithium salts. These electrolyte salts can be used singly or in combination of two or more of them.

The gelator and the gel obtained from the gelator of the present invention can be used for materials in various fields, such as cell culture base materials, base materials for preserving biomolecules such as cells and proteins, base materials for external use, base materials for biochemistry, base materials for food, contact lenses, disposable diapers, artificial actuators, and base materials for dryland farming. The gelator and the gel can also be widely used for bioreactor carriers for enzymes and other substances in studies, medicines, analysis, and various industries.

[Method for Producing Gelator]

The present invention also encompasses a method for producing the compound of Formula (1) or Formula (2) as the gelator of the present invention.

In other words, the production method is characterized by reacting a compound of Formula [A]:

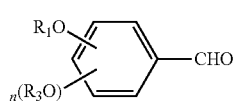

(where each of $R_1$ and $R_3$ is independently a linear or branched alkyl group having a carbon atom number of 1 to 20, a cyclic $C_{3-20}$ alkyl group, or a linear or branched alkenyl group having a carbon atom number of 2 to 20; and n is 0 or an integer of 1 to 4) with an acetalizing agent, and subsequently subjecting the obtained acetal derivative to annulation reaction with glucose, mannose, or a derivative thereof, thus producing the compound of Formula (1) or Formula (2), in which the reactions are carried out in a one-pot system in the presence of ethanol and p-toluenesulfonic acid.

EXAMPLES

Examples will be described below in order to further explain the feature of the present invention, but the present invention is not limited by these examples.

The signs shown in scheme A and schemes 1 to 10 below are signs given in the respective schemes and differ from the signs given in the detailed description of the invention and claims.

Reagents used as synthetic raw materials in examples are shown below. Methyl α-D-mannopyranoside, p-methoxybenzaldehyde, p-ethoxybenzaldehyde, p-(dodecyloxy)benzaldehyde, 4-bromo-1-butene, 1-bromo-3-methyl-2-butene, 1-bromobutane, 1-bromohexane, D(+)-glucose, and ethyl α-D-glucoside were purchased from Wako Pure Chemical Industries, Ltd. Methyl α-D-glucopyranoside, p-toluenesulfonic acid monohydrate, 4-propoxybenzaldehyde, 4-n-butoxybenzaldehyde, 4-n-pentyloxybenzaldehyde, 4-n-hexyloxybenzaldehyde, 4-n-octyloxybenzaldehyde, 4-n-decyloxybenzaldehyde, trimethyl orthoformate, bromocyclohexane, tetrabutylammonium iodide, triethyl orthoformate, 4-hydroxybenzaldehyde, 3-hydroxybenzaldehyde, vanillin, p-toluenesulfonic acid (anhydride), and 3,4-dimethoxybenzaldehyde were purchased from Tokyo Chemical Industry Co., Ltd. Copper(II) tetrafluoroborate hydrate, 2-ethylhexyl bromide, and geranyl bromide were purchased from. Sigma-Aldrich Japan.

N,N-dimethylformamide (DMF) (dehydrated, for organic synthesis), methanol (dehydrated, for organic synthesis), and ethanol (super dehydrated, for organic synthesis), which were used as reaction solvents, were purchased from Wako Pure Chemical Industries, Ltd.

Sodium sulfate (guaranteed reagent), sodium chloride (guaranteed reagent), sodium hydrogen carbonate (guaranteed reagent), and diethyl ether (guaranteed reagent), which were used for after treatment of reaction and purification, were purchased from Wako Pure Chemical Industries, Ltd. Hexane (guaranteed reagent), ethyl acetate (guaranteed reagent), chloroform (guaranteed reagent), and diisopropyl ether (guaranteed reagent), which were also used for after treatment of reaction and purification, were purchased from Kanto Chemical Co., Inc.

Deuterated chloroform (containing 0.03% TMS (tetramethylsilane)) and deuterated dimethylformamide, which were used for NMR measurement, were purchased from Sigma-Aldrich Japan.

Solvents used in gelation tests are shown below. Octane (guaranteed reagent), cyclohexane (guaranteed reagent), toluene (guaranteed reagent), ethanol (guaranteed reagent), olive oil, isopropyl myristate (extra pure reagent), glycerol (guaranteed reagent), squalane (extra pure reagent), squalene (guaranteed reagent), acetonitrile (guaranteed reagent), methanol (guaranteed reagent), propylene glycol (guaranteed reagent), 1,3-butanediol (another name: butylene glycol) (guaranteed reagent), and glycerin (guaranteed reagent) were purchased from Wako Pure Chemical Industries, Ltd. Ethylene glycol (guaranteed reagent) was purchased from Kanto Chemical Co., Inc. SH245 was purchased from Dow Corning Toray Co., Ltd. Pentylene glycol was purchased from ITO. Dimethyl sulfoxide (DMSO) was purchased from Tokyo Chemical Industry Co., Ltd. Water used was pure water.

Preservatives and surfactants used in gelation test are shown below.

Preservatives: Methylparaben and 2-phenoxyethanol (guaranteed reagent) were purchased from Wako Pure Chemical Industries, Ltd.

Surfactants: Polyoxyethylene sorbitan monolaurate (Tween 20), sodium dodecyl sulfate (SDS, extra pure reagent), stearyltrimethylammonium bromide (STAB), and 3-[(3-cholamidopropyl)dimethylammonio]propane-sulfonate (CHAPS) were purchased from Wako Pure Chemical Industries, Ltd.

Apparatuses and conditions used for various measurements and analyses are shown below.

(1) $^1$H-NMR spectrum
Apparatus: AVANCE 500, manufactured by Bruker BioSpin K. K.
JNM-ECA 600, manufactured by JEOL Ltd.
(2) High performance liquid chromatography (HPLC)
Apparatus: 1200 series, manufactured by Agilent Technologies, Inc.
(3) LC-MS
Apparatus: e2695 (LC), 2489 (UV), 3100 (MS), manufactured by Nihon Waters K. K.
(4) Optical microscope
Apparatus: DM 2500, manufactured by Leica Microsystems
(5) Confocal laser scanning microscope
Apparatus: LSM 700, manufactured by Carl Zeiss
(6) Scanning electron microscope (SEM)
Apparatus: SU 8000, manufactured by Hitachi High-Technologies Corporation
(7) Atomic force microscope (AFM)
Apparatus: Nanocute, manufactured by SII NanoTechnology Inc.
(8) Vortex mixer
Apparatus: Voltex Genie 2, manufactured by Scientific Industries
(9) Homogenizer
Apparatus: Omni Tip™ Homogenizing Kit, manufactured by Omni International Example 1

Synthesis of Gelator

Compounds to be mannose gelators and glucose gelators can be synthesized in accordance with scheme A shown below. Commercially available aromatic aldehyde compounds that have various hydrocarbon groups and are raw materials for the gelators were purchased (see the description above), and commercially unavailable aromatic aldehyde compounds were synthesized in accordance with scheme 1 described later.

The annulation reaction of the aromatic aldehyde compound and a sugar is typically carried out by annulation reaction of an acetal derived from the aldehyde or carried out by annulation reaction of the aldehyde in heating conditions. The present invention has another feature of one-step annulation reaction of the aromatic aldehyde compound at room temperature.

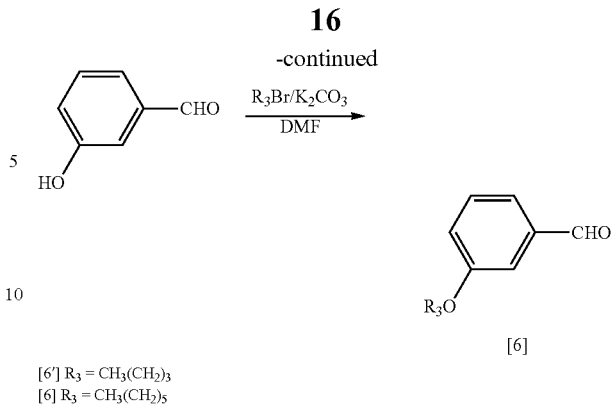

[6'] $R_3 = CH_3(CH_2)_3$
[6] $R_3 = CH_3(CH_2)_5$

Scheme A: Synthetic routes of one-step reaction and two step reaction

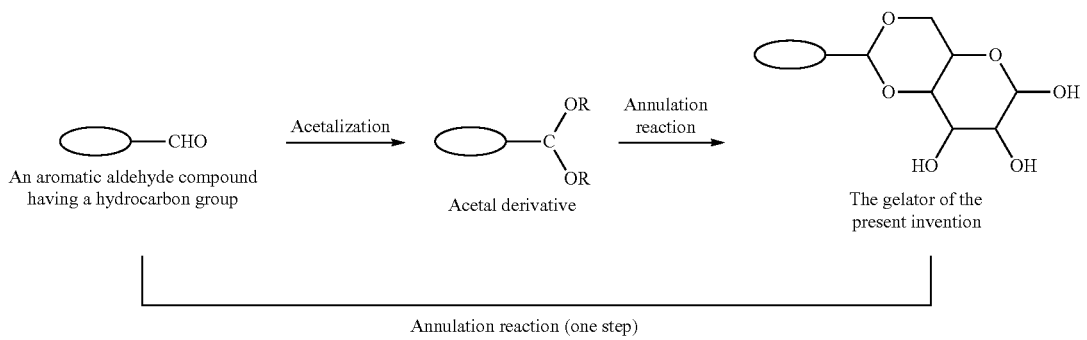

[Synthesis of Aromatic Aldehyde Compound Having Hydrocarbon Group]

In accordance with scheme 1 below, aromatic aldehyde compounds having various hydrocarbon groups were synthesized.

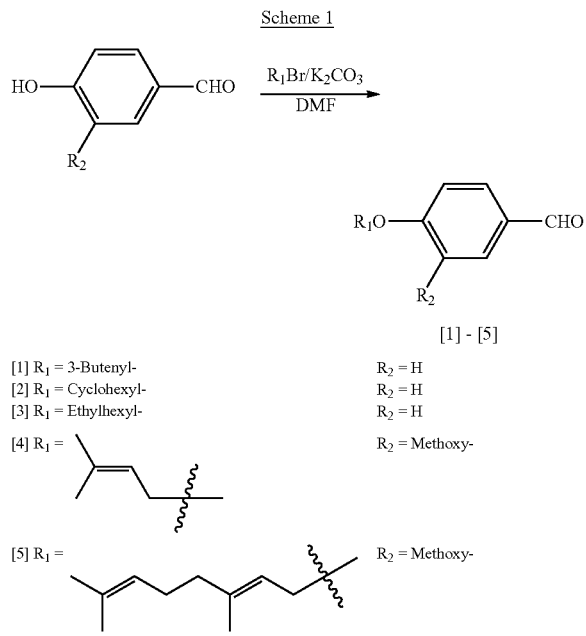

Synthesis of Compound [1]: Under a Nitrogen Atmosphere, p-hydroxybenzaldehyde (4.9 g, 40 mmol), 4-bromo-1-butene (8.1 g, 60 mmol), and potassium carbonate (8.3 g, 60 mmol) were added in 80 mL of dry N,N-dimethylformamide (DMF), and the whole was heated at 80° C. for 6 hours. The reaction solution was allowed to cool to room temperature, then insolubles were removed by filtration, and the filtrate was concentrated under reduced pressure. To the residue, ethyl acetate and saturated sodium chloride were added. The resultant mixture was subjected to a liquid separation operation, and the organic phase was extracted. The organic phase was washed with saturated sodium chloride. The organic phase was dried over sodium sulfate, then the sodium sulfate was filtered off, and the filtrate was concentrated under reduced pressure. The residue was purified by column chromatography (silica gel, hexane: ethyl acetate=9:1 (v/v)), yielding the target compound: Yield 91%; $^1$H NMR (500 MHz, CDCl$_3$): δ9.88 (s, 1H), 7.85-7.81 (m, 2H), 7.02-6.95 (m, 2H), 5.95-5.86 (m, 1H), 5.22-5.12 (m, 2H), 4.15-4.05 (m, 2H), 2.61-2.55 (m, 2H).

Synthesis of compound [2]: Under a nitrogen atmosphere, 4-hydroxybenzaldehyde (10.0 g, 82 mmol), bromocyclohexane (15.0 mL, 122 mmol), potassium carbonate (34.0 g, 246 mmol), and tetrabutylammonium iodide (0.25 g, 0.67 mmol) were added in 80 mL of dry N,N-dimethylformamide (DMF), and the whole was heated at 150° C. for 12 hours. The reaction solution was allowed to cool to room temperature, then insolubles were removed by filtration, and the filtrate was concentrated under reduced pressure. To the residue, ethyl acetate and saturated sodium chloride were added. The resultant mixture was subjected to a liquid separation operation, and the organic phase was extracted. The organic phase was washed with saturated sodium chloride. The organic phase was dried over sodium sulfate, then the sodium sulfate was filtered off, and the filtrate was concentrated under reduced pressure. The residue was purified by column chromatography (silica gel, hexane: ethyl acetate=9:1 (v/v)), yielding the target compound: Yield 12%; δ9.85 (s, 1H), 7.83-7.79 (m, 2H), 7.00-6.96 (m, 2H), 4.41-4.35 (m, 1H), 2.05-1.98 (m, 2H), 1.87-1.79 (m, 2H), 1.63-1.50 (m, 3H), 1.45-1.29 (m, 3H).

Synthesis of compound [3]: Under a nitrogen atmosphere, 4-hydroxybenzaldehyde (4.9 g, 40 mmol), 2-ethylhexyl bromide (9.7 g, 50 mmol), and potassium carbonate (8.3 g, 60 mmol) were added in 80 mL of dry N,N-dimethylformamide (DMF), and the whole was heated at 80° C. for 3 hours. The reaction solution was allowed to cool to room temperature, then insolubles were removed by filtration, and the filtrate was concentrated under reduced pressure. To the residue, ethyl acetate and saturated sodium chloride were added. The resultant mixture was subjected to a liquid separation operation, and the organic phase was extracted. The organic phase was washed with saturated sodium chloride. The organic phase was dried over sodium sulfate, then the sodium sulfate was filtered off, and the filtrate was concentrated under reduced pressure. The residue was purified by column chromatography (silica gel, hexane: ethyl acetate=9:1 (v/v)), yielding the target compound: Yield 95%; $^1$H NMR (500 MHz, CDCl$_3$): δ9.88 (s, 1H), 7.85-7.81 (m, 2H), 7.02-6.98 (m, 2H), 3.94-3.91 (m, 2H), 1.78-1.73 (m, 1H), 1.53-1.30 (m, 8H), 0.95-0.85 (m, 6H).

Synthesis of compound [4]: Under a nitrogen atmosphere, vanillin (3.9 g, 26 mmol), 1-bromo-3-methyl-2-butene (3.4 g, 23 mmol), and potassium carbonate (4.2 g, 30 mmol) were added in 50 mL of dry N,N-dimethylformamide (DMF), and the whole was heated at 50° C. for 3 hours. The reaction solution was allowed to cool to room temperature, then insolubles were removed by filtration, and the filtrate was concentrated under reduced pressure. The residue was purified by column chromatography (silica gel, hexane: ethyl acetate=9:1 to 7:3 (v/v)), yielding the target compound: Yield 75%; $^1$H NMR (500 MHz, CDCl$_3$): δ9.85 (s, 1H), 7.44 (d, 1H, J=8.2 Hz), 7.41 (s, 1H), 6.98 (d, 1H, J=8.2 Hz), 5.52 (t, 1H, J=6.8 Hz), 4.68 (d, 2H, J=6.6 Hz), 3.94 (s, 3H), 1.80 (s, 3H), 1.77 (s, 3H).

Synthesis of compound [5]: Under a nitrogen atmosphere, vanillin (1.9 g, 12 mmol), geranyl bromide (2.4 g, 11 mmol), and potassium carbonate (2.1 g, 15 mmol) were added in 20 mL of dry N,N-dimethylformamide (DMF), and the whole was heated at 80° C. for 3 hours. The reaction solution was allowed to cool to room temperature, then insolubles were removed by filtration, and the filtrate was concentrated under reduced pressure. The residue was purified by column chromatography (silica gel, hexane: ethyl acetate=10:0 to 6:4 (v/v)), yielding the target compound: Yield 75%; $^1$H NMR (500 MHz, CDCl$_3$): δ9.85 (s, 1H), 7.44 (d, 1H, J=8.2 Hz), 7.41 (s, 1H), 6.97 (d, 1H, J=8.2 Hz), 5.51 (t, 1H, J=6.5 Hz), 5.07 (t, 1H, J=7.0 Hz), 4.72 (d, 2H, J=6.3 kHz), 3.94 (s, 3H), 2.17-2.05 (m, 4H), 1.76 (s, 3H), 1.66 (s, 3H), 1.60 (s, 3H).

Compound [6]: Under a nitrogen atmosphere, 3-hydroxybenzaldehyde (4.9 g, 40 mmol), 1-bromohexane (7.3 g, 44 mmol), and potassium carbonate (6.9 g, 50 mmol) were added in 60 mL of dry N,N-dimethylformamide (DMF), and the whole was heated at 80° C. for 2 hours. The reaction solution was allowed to cool to room temperature, then insolubles were removed by filtration, and the filtrate was concentrated under reduced pressure. To the residue, ethyl acetate and saturated sodium chloride were added. The resultant mixture was subjected to a liquid separation operation, and the organic phase was extracted. The organic phase was washed with saturated sodium chloride. The organic phase was dried over sodium sulfate, then the sodium sulfate was filtered off, and the filtrate was concentrated under reduced pressure. The residue was purified by column chromatography (silica gel, hexane: ethyl acetate=10:0 to 7:3 (v/v)), yielding the target compound: Yield 97%; $^1$H NMR (500 MHz, CDCl$_3$): δ9.97 (s, 1H), 7.46-7.41 (m, 2H), 7.40-6.36 (m, 1H), 7.20-7.14 (m, 1H), 4.01 (t, 2H, J=6.5 Hz), 1.84-1.76 (m, 2H), 1.52-1.43 (m, 2H), 1.40-1.30 (m, 4H), 0.96-0.86 (m, 3H).

Synthesis of compound [6']: Under a nitrogen atmosphere, 3-hydroxybenzaldehyde (3.7 g, 30 mmol), 1-bromobutane (4.5 g, 33 mmol), and potassium carbonate (5.3 g, 38 mmol) were added in 30 mL of dry N,N-dimethylformamide (DMF), and the whole was heated at 80° C. for 2 hours. The reaction solution was allowed to cool to room temperature, then insolubles were removed by filtration, and the filtrate was concentrated under reduced pressure. The residue was purified by column chromatography (silica gel, hexane: ethyl acetate=10:0 to 9:1 (v/v)), yielding the target compound: Yield 95%; $^1$H NMR (500 MHz, CDCl$_3$): δ9.97 (s, 1H), 7.46-7.37 (m, 3H), 7.17 (s, 1H), 4.02 (t, 2H, J=6.6 Hz), 1.83-1.75 (m, 2H), 1.55-1.46 (m, 2H), 0.98 (t, 3H, J=7.5 Hz).

[Synthesis of Acetal Derivative]
<Dimethyl Acetalization Using Metal Catalyst (Copper(II) Tetrafluoroborate Hydrate) (Scheme 2)>

In accordance with scheme 2 below, aromatic aldehyde compounds were subjected to dimethyl acetalization, yielding acetal derivatives [17] to [32].

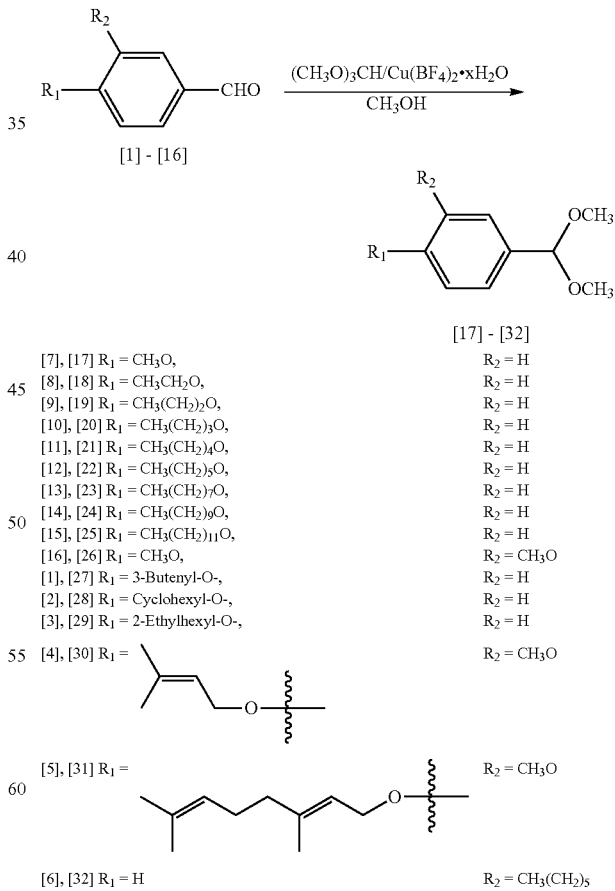

Synthesis of compound [17]: Under a nitrogen atmosphere, p-methoxybenzaldehyde[7] (2.7 g, 20 mmol) and trimethyl orthoformate (4.4 mL, 40 mmol) were dissolved in 8 mL of dry methanol, and to the solution, copper(II) tetrafluoroborate hydrate (48 mg) was added. The mixture was stirred at room temperature for 1 hour, and saturated sodium hydrogen carbonate was added to stop the reaction. To the solution, ethyl acetate was added to perform extraction and the organic phase was then washed with saturated sodium chloride. The organic phase was dried over sodium sulfate, then the sodium sulfate was filtered off, and the filtrate was concentrated under reduced pressure: Yield 99%; $^1$H NMR (500 MHz, CDCl$_3$): δ 7.36 (d, 2H, J=8.8 Hz), 6.89 (d, 2H, J=8.8 Hz), 5.35 (s, 1H), 3.81 (s, 3H), 3.31 (s, 6H).

Other compounds [18] to [32] were also synthesized in the same manner as for compound [17]. For these compounds, analysis data alone are shown below.

Compound [18]: Yield 94%; $^1$H NMR (500 MHz, CDCl$_3$): δ 7.35 (d, 2H, J=8.8 Hz), 6.88 (d, 2H, J=8.8 Hz), 5.35 (s, 1H), 4.04 (q, 2H, J=6.9 Hz), 3.31 (s, 6H), 1.41 (t, 3H, J=7.1 Hz).

Compound [19]: Yield 95%; $^1$H NMR (500 MHz, CDCl$_3$): δ 7.37 (d, 2H, J=8.2 Hz), 6.91 (d, 2H, J=8.8 Hz), 5.37 (s, 1H), 3.95 (t, 2H, J=6.5 Hz), 3.34 (s, 6H), 1.91-1.79 (m, 2H), 1.06 (t, 3H, J=7.5 Hz).

Compound [20]: Yield 99%; $^1$H NMR (500 MHz, CDCl$_3$): δ 7.35 (d, 2H, J=8.8 Hz), 6.89 (d, 2H, J=8.8 Hz), 5.35 (s, 1H), 3.96 (t, 2H, J=6.6 Hz), 3.31 (s, 6H), 1.80-1.73 (m, 2H), 1.54-1.44 (m, 2H), 0.97 (t, 3H, J=7.6 Hz).

Compound [21]: Yield 95%; $^1$H NMR (500 MHz, CDCl$_3$): δ 7.35 (d, 2H, J=8.8 Hz), 6.88 (d, 2H, J=8.5 Hz), 5.35 (s, 1H), 3.96 (t, 2H, J=6.6 Hz), 3.31 (s, 6H), 1.82-1.75 (m, 2H), 1.48-1.33 (m, 4H), 0.93 (t, 3H, J=7.1 Hz).

Compound [22]: Yield 99%; $^1$H NMR (500 MHz, CDCl$_3$): δ 7.35 (d, 2H, J=8.8 Hz), 6.88 (d, 2H, J=8.8 Hz), 5.35 (s, 1H), 3.95 (t, 2H, J=6.6 Hz), 3.31 (s, 6H), 1.81-1.74 (m, 2H), 1.51-1.41 (m, 2H), 1.39-1.29 (m, 4H), 0.94-0.87 (m, 3H).

Compound [23]: Yield 99%; $^1$H NMR (500 MHz, CDCl$_3$): δ 7.35 (d, 2H, J=8.8 Hz), 6.88 (d, 2H, J=8.8 Hz), 5.35 (s, 1H), 3.95 (t, 2H, J=6.6 Hz), 3.31 (s, 6H), 1.82-1.73 (m, 2H), 1.50-1.40 (m, 2H), 1.39-1.22 (m, 8H), 0.92-0.85 (m, 3H).

Compound [24]: Yield 98%; $^1$H NMR (500 MHz, CDCl$_3$): δ 7.34 (d, 2H, J=8.8 Hz), 6.88 (d, 2H, J=8.8 Hz), 5.34 (s, 1H), 3.95 (t, 2H, J=6.6 Hz), 3.31 (s, 6H), 1.82-1.73 (m, 2H), 1.50-1.40 (m, 2H), 1.39-1.20 (m, 12H), 0.92-0.85 (m, 3H).

Compound [25]: Yield 99%; $^1$H NMR (500 MHz, CDCl$_3$): δ 7.35 (d, 2H, J=8.8 Hz), 6.88 (d, 2H, J=8.8 Hz), 5.35 (s, 1H), 3.95 (t, 2H, J=6.6 Hz), 3.31 (s, 6H), 1.81-1.73 (m, 2H), 1.49-1.40 (m, 2H), 1.39-1.20 (m, 16H), 0.88 (t, 3H, J=6.9 Hz).

Compound [26]: Yield 97%; $^1$H NMR (500 MHz, CDCl$_3$): δ 7.02-6.97 (m, 2H), 6.88-6.84 (m, 1H), 5.33 (s, 1H), 3.90 (s, 3H), 3.89 (s, 3H), 3.33 (s, 6H).

Compound [27]: Yield 75%; $^1$H NMR (500 MHz, CDCl$_3$): δ 7.37-7.33 (m, 2H), 6.92-6.87 (m, 2H), 5.96-5.85 (m, 1H), 5.35 (s, 1H), 5.21-5.08 (m, 2H), 4.02 (t, 2H, J=6.6 Hz), 3.31 (s, 6H), 2.58-2.51 (m, 2H).

Compound [28]: Yield 98%; $^1$H NMR (500 MHz, CDCl$_3$): δ 7.33 (d, 2H, J=8.8 Hz), 6.88 (d, 2H, J=8.8 Hz), 5.33 (s, 1H), 4.31-4.23 (m, 1H), 3.32 (s, 6H), 2.03-1.92 (m, 2H), 1.86-1.73 (m, 2H), 1.64-1.23 (m, 6H).

Compound [29]: Yield 97%; $^1$H NMR (500 MHz, CDCl$_3$): δ 7.37-7.33 (m, 2H), 6.92-6.87 (m, 2H), 5.35 (s, 1H), 3.87-3.80 (m, 2H), 3.31 (s, 6H), 1.77-1.67 (m, 1H), 1.55-1.25 (m, 8H), 0.96-0.86 (m, 6H).

Compound [30]: Yield 96%; $^1$H NMR (500 MHz, CDCl$_3$): δ6.98 (s, 1H), 6.96 (d, 1H, J=8.2 Hz), 6.86 (d, 1H, J=8.2 Hz), 5.52 (t, 1H, J=6.6 Hz), 5.33 (s, 1H), 4.59 (d, 2H, J=6.6 Hz), 3.88 (s, 3H), 3.33 (s, 6H), 1.77 (s, 3H), 1.73 (s, 3H).

Compound [31]: Yield 98%; NMR (500 MHz, CDCl$_3$): δ6.98 (s, 1H), 6.95 (d, 1H, J=7.9 Hz), 6.85 (d, 1H, J=7.9 Hz), 5.51 (s, 1H), 5.31 (s, 1H), 5.08 (s, 1H), 4.62 (d, 2H, J=6.0 Hz), 3.88 (s, 3H), 3.33 (s, 6H), 2.15-2.02 (m, 4H), 1.72 (s, 3H), 1.67 (s, 1H), 1.59 (s, 3H), 1.80-1.52 (m, 9H).

Compound [32]: Yield 97%; $^1$H NMR (500 MHz, CDCl$_3$): δ 7.32-7.26 (m, 1H), 7.06-7.02 (m, 2H), 6.91-6.86 (m, 1H), 5.38 (s, 1H), 3.99 (t, 2H, J=6.6 Hz), 3.36 (s, 6H), 1.85-1.76 (m, 2H), 1.54-1.44 (m, 2H), 1.42-1.32 (m, 4H), 0.98-0.91 (m, 3H).

<Dimethyl Acetalization Using p-Toluenesulfonic Acid as a Catalyst (Scheme 3)>

In accordance with scheme 3, an aromatic aldehyde compound was subjected to dimethyl acetalization, yielding acetal derivative [21].

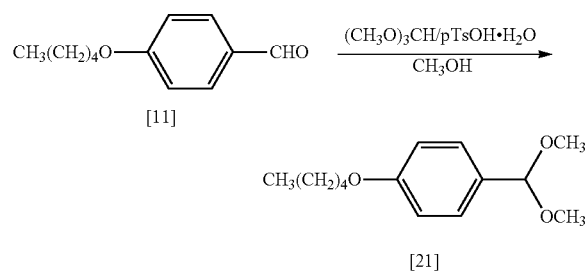

Scheme 3

Synthesis of compound [21]: Under a nitrogen atmosphere, 4-n-pentyloxybenzaldehyde[11] (1.9 g, 10 mmol) and trimethyl orthoformate (2.2 mL, 20 mmol) were dissolved in 4 mL of dry methanol, and to the solution, p-toluenesulfonic acid monohydrate (8 mg) was added. The mixture was stirred at room temperature for 1 hour, and saturated sodium hydrogen carbonate was added to stop the reaction. To the solution, ethyl acetate was added to perform extraction and the organic phase was then washed with saturated sodium chloride. The organic phase was dried over sodium sulfate, then the sodium sulfate was filtered off, and the filtrate was concentrated under reduced pressure: Yield 94%.

<Diethyl Acetalization Using p-Toluenesulfonic Acid as a Catalyst (Scheme 4)>

In accordance with scheme 4 below, aromatic aldehyde compounds were subjected to diethyl acetalization, yielding acetal derivatives [20'] and [21'].

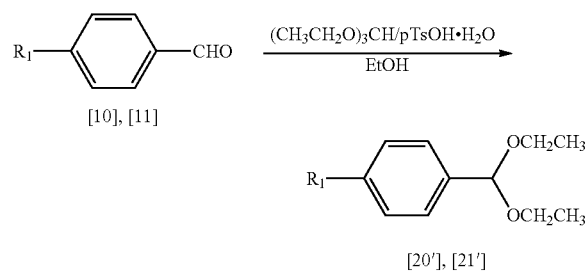

Scheme 4

[10], [20'] R$_1$ = CH$_3$(CH$_2$)$_3$O,
[11], [21'] R$_1$ = CH$_3$(CH$_2$)$_4$O,

Synthesis of compound [20']: Under a nitrogen atmosphere, 4-n-butoxybenzaldehyde[10] (2.5 g, 14 mmol) and triethyl orthoformate (5.0 mL, 38 mmol) were dissolved in 10 mL of dry ethanol, and to the solution, p-toluenesulfonic acid monohydrate (7 mg) was added. The mixture was stirred at room temperature for 1 hour, and saturated sodium hydrogen carbonate was added to stop the reaction. To the solution, ethyl acetate was added to perform extraction and the organic phase was then washed with saturated sodium chloride. The organic phase was dried over sodium sulfate, then the sodium sulfate was filtered off, and the filtrate was concentrated under reduced pressure: Yield 78%; NMR (500 MHz, CDCl$_3$): δ 7.37 (d, 2H, J=8.8 Hz), 6.88 ((d, 2H, J=8.8 Hz), 3.96 (t, 2H, J=6.5 Hz), 3.63-3.57 (m, 2H), 3.54-3.48 (m, 2H), 1.80-1.72 (m, 2H), 1.54-1.44 (m, 2H), 1.23 (t, 6H, J=7.1 Hz), 0.97 (t, 3H, J=7.5 Hz).

Synthesis of compound [21']: Under a nitrogen atmosphere, 4-n-pentyloxybenzaldehyde[11] (1.9 g, 10 mmol) and triethyl orthoformate (3.4 mL, 20 mmol) were dissolved in 4 mL of dry ethanol, and to the solution, p-toluenesulfonic acid monohydrate (8 mg) was added. The mixture was stirred at room temperature for 1 hour, and saturated sodium hydrogen carbonate was added to stop the reaction. To the solution, ethyl acetate was added to perform extraction and the organic phase was then washed with saturated sodium chloride. The organic phase was dried over sodium sulfate, then the sodium sulfate was filtered off, and the filtrate was concentrated under reduced pressure: Yield 95%; $^1$H NMR (500 MHz, CDCl$_3$): δ 7.37 (d, 2H, J=8.5 Hz), 6.87 (d, 2H, J=8.5 Hz), 5.46 (s, 1H), 3.95 (t, 2H, J=6.7 Hz), 3.64-3.57 (m, 2H), 3.55-3.47 (m, 2H), 1.81-1.74 (m, 2H), 1.47-1.33 (m, 4H), 1.23 (t, 6H, J=7.1 Hz), 0.93 (t, 3H, J=7.1 Hz).

[Synthesis of Gelator Compound from Acetal Derivative]
<Synthesis of mannose gelator from dimethyl acetal derivative>

In accordance with scheme 5 below, dimethyl acetal derivatives were reacted with methyl α-D-mannopyranoside, yielding compounds [M1] to [M10] as mannose gelators.

Scheme 5

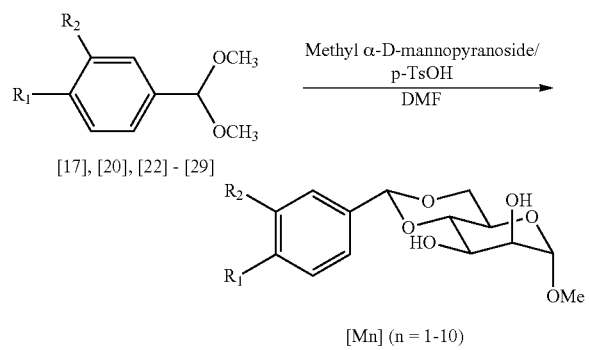

[17], [20], [22] - [29]

[Mn] (n = 1-10)

[17], [M1] R$_1$ = CH$_3$O, R$_2$ = H
[20], [M2] R$_1$ = CH$_3$(CH$_2$)$_3$O, R$_2$ = H
[22], [M3] R$_1$ = CH$_3$(CH$_2$)$_5$O, R$_2$ = H
[23], [M4] R$_1$ = CH$_3$(CH$_2$)$_7$O, R$_2$ = H
[24], [M5] R$_1$ = CH$_3$(CH$_2$)$_9$O, R$_2$ = H
[25], [M6] R$_1$ = CH$_3$(CH$_2$)$_{11}$O, R$_2$ = H
[26], [M7] R$_1$ = CH$_3$O, R$_2$ = CH$_3$O
[27], [M8] R$_1$ = 3-Butenyl-O-, R$_2$ = H
[28], [M9] R$_1$ = Cyclohexyl-O-, R$_2$ = H
[29], [M10] R$_1$ = 2-Ethylhexyl-O-, R$_2$ = H Synthesis of compound [M1]: Under a nitrogen atmosphere, to a solution of methyl α-D-mannopyranoside (4.3 g, 22 mmol) in DMF (20 mL), p-toluenesulfonic acid (190 mg, 0.5 mmol) was added, and the mixed solution was stirred at room temperature for 5 minutes. To the mixed solution, a solution of 4-methoxybenzaldehyde dimethyl acetal [17] (2.7 g, 20 mmol) in DMF (10 mL) was added dropwise at room temperature. After the dropwise addition, the mixed solution was stirred at room temperature for 10 minutes and stirred under reduced pressure for 2 hours. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diisopropyl ether, yielding the target compound as a white solid: Yield 55%; $^1$H NMR (600 MHz, CDCl$_3$): δ 7.44-7.39 (m, 2H), 6.92-6.87 (m, 2H), 5.52 (s, 1H), 4.75 (s, 1H), 4.30-4.22 (m, 1H), 4.07-4.00 (m, 2H), 3.93-3.86 (m, 1H), 3.85-3.76 (m, 5H), 3.40 (s, 3H), 2.66 (br, 2H).

Other compounds [M2] to [M10] were also synthesized in the same manner. For these compounds, analysis data alone are shown below.

Compound [M2]: Yield 45%; $^1$H NMR (600 MHz, CDCl$_3$): δ 7.42-7.37 (m, 2H), 6.91-6.86 (m, 2H), 5.52 (s, 1H), 4.76 (d, 1H, J=2.4 Hz), 4.30-4.23 (m, 1H), 4.09-4.02 (m, 2H), 3.96 (t, 2H, J=6.6 Hz), 3.93-3.86 (m, 1H), 3.85-3.76 (m, 2H), 3.40 (s, 3H), 2.64-2.56 (m, 2H), 1.79-1.72 (m, 2H), 1.52-1.44 (m, 2H), 0.97 (t, 3H, J=7.6 Hz).

Compound [M3]: Yield 49%; $^1$H NMR (600 MHz, CDCl$_3$): δ 7.39 (d, 2H, J=8.8 Hz), 6.89 (d, 2H, J=8.8 Hz), 5.52 (s, 1H), 4.76 (s, 1H), 4.30-4.22 (m, 1H), 4.08-4.02 (m, 2H), 3.98-3.93 (m, 2H), 3.92-3.86 (m, 1H), 3.84-3.76 (m, 2H), 3.40 (s, 3H), 2.64-2.59 (br, 2H), 1.81-1.73 (m, 21), 1.48-1.40 (m, 2H), 1.38-1.29 (m, 4H), 0.93-0.86 (m, 3H).

Compound [M4]: Yield 48%; $^1$H NMR (600 MHz, CDCl$_3$): δ 7.39 (d, 211, J=8.8 Hz), 6.88 (d, 2H, J=8.8 Hz), 5.52 (s, 1H), 4.76 (s, 1H), 4.30-4.23 (m, 1H), 4.08-4.02 (m, 2H), 3.98-3.86 (m, 3H), 3.85-3.76 (m, 2H), 3.40 (s, 3H), 2.65-2.59 (br, 2H), 1.80-1.73 (m, 2H), 1.47-1.40 (m, 2H), 1.37-1.22 (m, 8H), 0.92-0.85 (m, 3H).

Compound [M5]: Yield 43%; $^1$H NMR (600 MHz, CDCl$_3$): δ 7.39 (d, 2H, J=8.8 Hz), 6.88 (d, 2H, J=8.8 Hz), 5.52 (s, 1H), 4.76 (d, 1H, J=2.4 Hz), 4.30-4.22 (m, 1H), 4.08-4.01 (m, 2H), 3.97-3.86 (m, 3H), 3.84-3.76 (m, 2H), 3.40 (s, 3H), 2.65-2.56 (br, 2H), 1.80-1.73 (m, 2H), 1.47-1.39 (m, 2H), 1.37-1.21 (m, 12H), 0.88 (t, 3H, J=6.9 Hz).

Compound [M6]: Yield 41%; $^1$H NMR (600 MHz, CDCl$_3$): δ 7.42-7.36 (m, 2H), 6.91-6.85 (m, 2H), 5.51 (s, 1H), 4.75 (s, 1H), 4.29-4.22 (m, 1H), 4.08-4.01 (m, 2H), 3.97-3.85 (m, 3H), 3.84-3.76 (m, 2H), 3.40 (s, 3H), 2.68-2.63 (br, 2H), 1.80-1.72 (m, 2H), 1.57-1.39 (m, 2H), 1.38-1.20 (m, 16H), 0.88 (t, 3H, J=6.9 Hz).

Compound [M7]: Yield 32%; $^1$H NMR (600 MHz, CDCl$_3$): δ 7.05-7.01 (m, 2H), 6.85 (d, 1H, J=7.9 Hz), 5.52 (s, 1H), 4.75 (s, 1H), 4.32-4.24 (m, 1H), 4.08-4.01 (m, 2H), 3.91-3.85 (m, 7H), 3.83-3.76 (m, 2H) 3.40 (s, 3H), 2.89-2.71 (m, 2H).

Compound [M8]: Yield 45%; $^1$H NMR (600 MHz, CDCl$_3$): δ 7.40 (d, 211, J=8.6 Hz), 6.89 (d, 2H, J=8.8 Hz), 5.93-5.85 (m, 1H), 5.51 (s, 1H), 5.18-5.13 (m, 1H), 5.12-5.08 (m, 1H), 4.73 (s, 1H), 4.29-4.21 (m, 1H), 4.06-3.98 (m, 4H), 3.91-3.85 (m, 1H), 3.83-3.75 (m, 2H), 3.39 (s, 3H), 2.81-2.78 (m, 1H), 2.77-2.75 (m, 1H), 2.56-2.50 (m, 2H).

Compound [M9]: Yield 31%; $^1$H NMR (600 MHz, CDCl$_3$): δ 7.38 (d, 2H, J=8.6 Hz), 6.88 (d, 2H, J=8.8 Hz), 5.50 (s, 1H), 4.74 (s, 1H), 4.28-4.21 (m, 1H), 4.06-3.99 (m, 2H), 3.91-3.85 (m, 1H), 3.83-3.75 (m, 2H), 3.39 (s, 3H), 2.76 (d, 1H, J=3.4 Hz), 2.73 (d, 1H, J=2.2 Hz), 2.01-1.90 (m, 2H), 1.82-1.74 (m, 2H), 1.60-1.45 (m, 3H), 1.40-1.25 (m, 3H).

Compound [M10]: Yield 40%; $^1$H NMR (600 MHz, CDCl$_3$): δ 7.39 (d, 2H, J=8.6 Hz), 6.88 (d, 2H, J=8.6 Hz), 5.50 (s, 1H), 4.69 (s, 1H), 4.27-4.20 (m, 1H), 4.03-3.94 (m, 2H), 3.89-3.74 (m, 5H), 3.37 (s, 3H), 3.05 (d, 1H, J=2.9 Hz), 3.00 (s, 1H), 1.74-1.67 (m, 1H), 1.53-1.24 (m, 8H), 0.94-0.87 (m, 6H).

<Synthesis of Glucose Gelator from Dimethyl Acetal Derivative>

In accordance with scheme 6 below, dimethyl acetal derivatives were reacted with methyl α-D-glucopyranoside, yielding compounds [G1] to [G9] and [G11] to [G13] as glucose gelators.

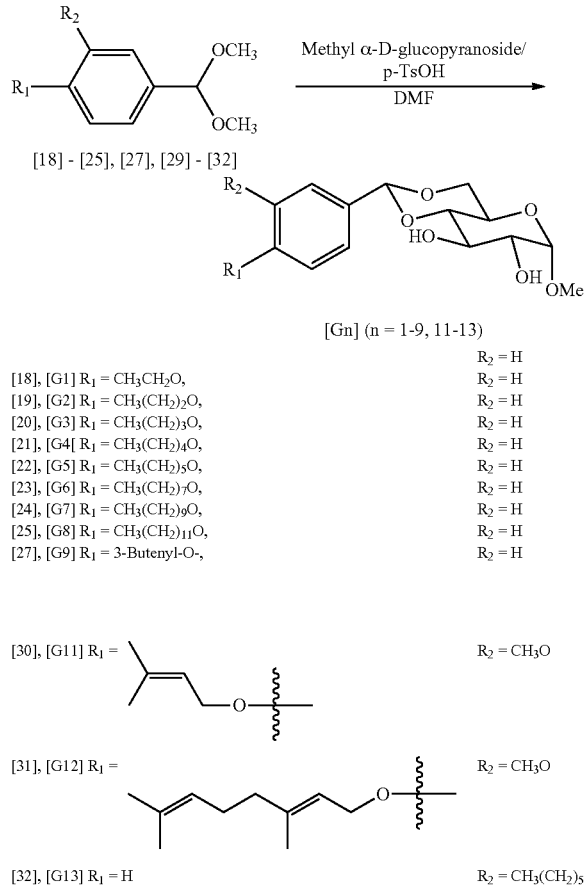

Synthesis of compound [G1]: Under a nitrogen atmosphere, to a solution of methyl α-D-glucopyranoside (2.5 g, 13 mmol) in DMF (10 mL), p-toluenesulfonic acid (59 mg, 0.3 mmol) was added, and the mixed solution was stirred at room temperature for 5 minutes. To the mixed solution, a solution of 4-ethoxybenzaldehyde dimethyl acetal [18] (2.3 g, 12 mmol) in DMF (5 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diethyl ether, yielding the target compound as a white solid: Yield 50%; $^1$H NMR (500 MHz, CDCl$_3$): δ 7.40 (d, 2H, J=8.8 Hz), 6.88 (d, 2H, J=8.5 Hz), 5.49 (s, 1H), 4.81 (s, 1H), 4.28 (d, 1H, 10.0 Hz), 4.03 (q, 2H, J=6.9 Hz), 3.93 (t, 1H, J=9.2 Hz), 3.80 (t, 1H, J=9.8 Hz), 3.73 (t, 1H, 10.1 Hz), 3.64 (t, 1H, J=9.3 Hz), 3.51-3.46 (m, 4H), 2.63 (s, 1H), 2.21 (d, 1H, J=9.4 Hz), 1.40 (t, 3H, J=6.9 Hz).

Synthesis of compound [G2]: Under a nitrogen atmosphere, to a solution of methyl α-D-glucopyranoside (2.9 g, 15 mmol) in DMF (15 mL), p-toluenesulfonic acid (63 mg, 0.3 mmol) was added, and the mixed solution was stirred at room temperature for 5 minutes. To the mixed solution, a solution of 4-propoxybenzaldehyde dimethyl acetal[19] (2.9 g, 14 mmol) in DMF (8 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diisopropyl ether, yielding the target compound as a white solid: Yield 66%; $^1$H NMR (500 MHz, CDCl$_3$): δ 7.40 (d, 2H, J=8.5 Hz), 6.88 (d, 2H, J=8.9 Hz), 5.49 (s, 1H), 4.81 (s, 1H), 4.28 (d, 1H, J=9.9 Hz), 3.96-3.89 (m, 3H), 3.80 (t, 1H, J=9.8 Hz), 3.73 (t, 1H, J=10 Hz), 3.64 (t, 1H, J=9.4 Hz), 3.51-3.46 (m, 4H), 2.65 (s, 1H), 2.22 (d, 1H, J=9.4 Hz), 1.84-1.75 (m, 2H), 1.02 (t, 3H, J=7.5 Hz).

Synthesis of compound [G3]: Under a nitrogen atmosphere, to a solution of methyl α-D-glucopyranoside (4.3 g, 22 mmol) in DMF (20 mL), p-toluenesulfonic acid (190 mg, 0.5 mmol) was added, and the mixed solution was stirred at room temperature for 5 minutes. To the mixed solution, a solution of 4-butoxybenzaldehyde dimethyl acetal [20] (4.7 g, 21 mmol) in DMF (10 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diethyl ether, yielding the target compound as a white solid: Yield 85%; $^1$H NMR (500 MHz, CDCl$_3$): δ 7.40 (d, 2H, J=8.8 Hz), 6.88 (d, 2H, J=8.8 Hz), 5.49 (s, 1H), 4.81 (d, 1H, J=3.8 Hz), 4.28 (dd, 1H, J=9.8, 4.4 Hz), 3.97-3.91 (m, 3H), 3.83-3.70 (m, 2H), 3.64 (dt, 1H, J=9.5, 4.1 Hz), 3.50-3.47 (m, 4H), 2.67 (s, 1H), 124 (d, 1H, J=9.5 Hz), 1.75 (m, 2H), 1.48 (sext, 2H, J=7.6 Hz), 0.96 (t, 3H, J=7.6 Hz).

Synthesis of compound [G4]: Under a nitrogen atmosphere, to a solution of methyl α-D-glucopyranoside (2.7 g, 14 mmol) in DMF (12 mL), p-toluenesulfonic acid (59 mg, 0.3 mmol) was added, and the mixed solution was stirred at room temperature for 5 minutes. To the mixed solution, a solution of 4-pentyloxybenzaldehyde dimethyl acetal[21] (3.0 g, 13 mmol) in DMF (6 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diisopropyl ether, yielding the target compound as a white solid: Yield 60%; $^1$H NMR (500 MHz, CDCl$_3$): δ 7.40 (d, 2H, J=8.8 Hz), 6.88 (d, 2H, J=8.9 Hz), 5.49 (s, 1H), 4.81 (s, 1H), 4.28 (d, 1H, J=10.0 Hz), 3.97-3.90 (m, 3H), 3.80 (t, 1H, J=9.9 Hz), 3.73 (t, 1H, J=10.3 Hz), 3.64 (t, 1H, J=9.4 Hz), 3.52-3.45 (m, 4H), 2.66 (s, 1H), 2.23 (d, 1H, J=9.7 Hz), 1.81-1.73 (m, 2H), 1.47-1.32 (m, 4H), 0.92 (t, 3H, J=7.3 Hz).

Synthesis of compound [G5]: Under a nitrogen atmosphere, to a solution of methyl α-D-glucopyranoside (2.1 g, 11 mmol) in DMF (10 mL), p-toluenesulfonic acid (98 mg, 0.5 mmol) was added, and the mixed solution was stirred at room temperature for 5 minutes. To the mixed solution, a solution of 4-hexyloxybenzaldehyde dimethyl acetal[22] (2.5 g, 10 mmol) in DMF (5 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diethyl ether, yielding the target compound as a white solid: Yield 72%; $^1$H NMR (500 MHz, CDCl$_3$): δ 7.40 (d, 2H, J=8.8 Hz), 6.88 (d, 2H, J=8.9 Hz), 5.49 (s, 1H), 4.81 (s, 1H), 4.28 (d, 1H, J=9.9 Hz), 3.97-3.90 (m, 3H), 3.80 (t, 1H, J=9.9 Hz), 3.73 (t, 1H, J=10.3 Hz), 3.64 (t, 1H, J=9.4 Hz), 3.51-3.45 (m, 4H), 2.61 (s, 1H), 2.20 (d, 1H, J=9.5 Hz), 1.81-1.72 (m, 2H), 1.48-1.40 (m, 2H), 1.38-1.30 (m, 4H), 0.90 (t, 3H, J=7.1 Hz).

Compound [G6]: Under a nitrogen atmosphere, to a solution of methyl α-D-glucopyranoside (4.3 g, 22 mmol) in DMF (20 mL), p-toluenesulfonic acid (190 mg, 1.0 mmol) was added, and the mixed solution was stirred at room temperature for 5 minutes. To the mixed solution, a solution of 4-octyloxybenzaldehyde dimethyl acetal [23] (5.6 g, 20 mmol) in DMF (10 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diethyl ether, yielding the target compound as a white solid: Yield 63%; $^1$H NMR (500 MHz, CDCl$_3$): δ 7.40 (d, 2H, J=8.8 Hz), 6.88 (d, 2H, J=8.8 Hz), 5.49 (s, 1H), 4.80 (d, 1H, J=3.5 Hz), 4.28 (dd, 1H, J=10.1, 4.8 Hz), 3.97-3.89 (m, 3H), 3.83-3.70 (m, 2H), 3.67-3.61 (m, 1H), 3.51-3.45 (m, 4H), 2.64 (d, 1H, J=2.2 Hz), 2.22 (d, 1H, J=9.4 Hz), 1.80-1.72 (m, 2H), 1.48-1.22 (m, 10H), 0.93-0.85 (m, 3H).

Synthesis of compound [G7]: Under a nitrogen atmosphere, to a solution of methyl α-D-glucopyranoside (0.9 g, 4.6 mmol) in DMF (4 mL), p-toluenesulfonic acid (40 mg, 0.2 mmol) was added, and the mixed solution was stirred at room temperature for 5 minutes. To the mixed solution, a solution of 4-decyloxybenzaldehyde dimethyl acetal[24] (1.3 g, 4.2 mmol) in DMF (2 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diethyl ether, yielding the target compound as a white solid: Yield 54%; $^1$H NMR (500 MHz, CDCl$_3$): δ 7.39 (d, 2H, J=8.9 Hz), 6.88 (d, 2H, J=8.8 Hz), 5.49 (s, 1H), 4.80 (s, 1H), 4.28 (d, 1H, J=9.9 Hz), 3.97-3.89 (m, 3H), 3.79 (t, J=9.8 Hz), 3.73 (t, 1H, J=10.1 Hz), 3.63 (t, 1H, J=9.4 Hz), 3.51-3.45 (m, 4H), 2.64 (s, 1H), 2.22 (d, 1H, J=9.7 Hz), 1.81-1.72 (m, 2H), 1.48-1.39 (m, 2H), 1.38-1.21 (m, 12H), 0.88 (t, 3H, J=6.9 Hz).

Compound [G8]: Under a nitrogen atmosphere, to a solution of methyl α-D-glucopyranoside (4.3 g, 22 mmol) in DMF (20 mL), p-toluenesulfonic acid (190 mg, 1.0 mmol) was added, and the mixed solution was stirred at room temperature for 5 minutes. To the mixed solution, a solution of 4-dodecyloxybenzaldehyde dimethyl acetal[25] (6.8 g, 20 mmol) in DMF (10 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diethyl ether, yielding the target compound as a white solid: Yield 33%; $^1$H NMR (500 MHz, CDCl$_3$): δ 7.39 (d, 2H, J=8.8 Hz), 6.88 (d, 2H, J=8.8 Hz), 5.49 (s, 1H), 4.81 (d, 1H, J=4.1 Hz), 4.28 (dd, 1H, J=9.8, 4.4 Hz), 3.97-3.90 (m, 3H), 3.83-3.77 (m, 1H), 3.73 (d, 1H, J=10.1 Hz), 3.64 (dt, 114, J=9.2, 4.1 Hz), 3.51-3.45 (m, 4H), 2.66 (s, 1H), 2.23 (d, 1H, J=9.5 Hz), 1.80-1.72 (m, 2H), 1.47-1.39 (m, 2H), 1.37-1.20 (m, 16H), 0.88 (t, 3H, J=6.9 Hz).

Synthesis of compound [G9]: Under a nitrogen atmosphere, to a solution of methyl α-D-glucopyranoside (2.4 g, 13 mmol) in DMF (10 mL), p-toluenesulfonic acid (55 mg, 0.3 mmol) was added, and the mixed solution was stirred at room temperature for 5 minutes. To the mixed solution, a solution of 4-(3-butenyloxy)benzaldehyde dimethyl acetal [27] (2.5 g, 11 mmol) in DMF (5 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diethyl ether, yielding the target compound as a white solid: Yield 81%; $^1$H NMR (500 MHz, CDCl$_3$): δ 7.40 (d, 2H, J=8.5 Hz), 6.89 (d, 2H, J=8.9H), 5.94-5.84 (m, 1H), 5.49 (s, 1H), 5.16 (d, 1H, J=17.0 Hz), 5.10 (d, 1H, J=10.0 Hz), 4.81 (s, 1H), 4.28 (d, 1H, J=9.9 Hz), 4.01 (t, 2H, J=6.6 Hz), 3.93 (t, 1H, J=9.2 Hz), 3.80 (t, 1H, J=9.8 Hz), 3.73 (t, 1H, J=10.2 Hz), 3.64 (t, 1H, J=9.3 Hz), 3.52-3.45 (m, 4H), 2.63 (s, 1H), 2.53 (q, 2H, J=6.7 Hz), 2.21 (d, 1H, J=9.5 Hz).

Synthesis of compound [G11]: Under a nitrogen atmosphere, to a solution of methyl α-D-glucopyranoside (2.5 g, 13 mmol) in DMF (13 mL), p-toluenesulfonic acid (58 mg, 0.3 mmol) was added, and the mixed solution was stirred at room temperature for 5 minutes. To the mixed solution, a solution of 3-methoxy-4-dimethylallyloxybenzaldehyde dimethyl acetal[30] (3.1 g, 12 mmol) in DMF (6 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diisopropyl ether, yielding the target compound as a white solid: Yield 58%; $^1$H NMR (500 MHz, CDCl$_3$): δ 7.03 (s, 1H), 7.00 (d, 1H, J=8.2 Hz), 6.86 (d, 1H, J=8.2 Hz), 5.52-5.47 (m, 2H), 4.82 (d, 1H, 3.8 Hz), 4.58 (d, 2H, J=6.6 Hz), 4.29 (q, 1H, J=5.0 Hz), 3.95 (t, 1H, J=9.2 Hz), 3.89 (s, 3H), 3.82 (t, 1H, J=10.0 Hz), 3.74 (t, 1H, J=10.3 Hz), 3.65 (t, 1H, J=9.4 Hz), 3.50-3.47 (m, 4H), 2.68 (s, 1H), 2.24 (d, 1H, J=9.5 Hz), 1.76 (s, 3H), 1.72 (s, 3H).

Synthesis of compound [G12]: Under a nitrogen atmosphere, to a solution of methyl α-D-glucopyranoside (1.9 g, 10 mmol) in DMF (10 mL), p-toluenesulfonic acid (45 mg, 0.2 mmol) was added, and the mixed solution was stirred at room temperature for 5 minutes. To the mixed solution, a solution of 3-methoxy-4-geranyloxybenzaldehyde dimethyl acetal[31] (3.0 g, 9 mmol) in DMF (5 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diisopropyl ether, yielding the target compound as a white solid: Yield 58%; $^1$H NMR (500 MHz, CDCl$_3$): δ 7.03 (s, 1H), 7.00 (d, 1H, J=8.2 Hz), 6.85 (d, 1H, J=8.2 Hz), 5.48 (s, 1H), 5.08 (t, 1H, J=6.8 Hz), 4.81 (d, 1H, J=3.7 Hz), 4.61 (d, 2H, J=6.3 Hz), 4.29 (q, 1H, J=4.9 Hz), 3.94 (t, 1H, J=9.3 Hz), 3.89 (s, 3H), 3.87-3.79 (m, 1H), 3.74 (t, 1H, J=10.3 Hz), 3.65 (t, 1H, J=9.4 Hz), 3.52-3.46 (m, 4H), 2.71 (s, 1H), 2.26 (d, 1H, J=9.4 Hz), 2.14-2.01 (m, 4H), 1.72 (s, 3H), 1.67 (s, 3H), 1.60 (s, 4H).

Compound [G13]: Under a nitrogen atmosphere, to a solution of methyl α-D-glucopyranoside (2.1 g, 11 mmol) in DMF (10 mL), p-toluenesulfonic acid (95 mg, 0.5 mmol) was added, and the mixed solution was stirred at room temperature for 5 minutes. To the mixed solution, a solution of 3-hexyloxybenzaldehyde dimethyl acetal [32] (2.5 g, 10 mmol) in DMF (5 mL) was added dropwise at room temperature. After the dropwise addition, the mixed solution was stirred at room temperature for 10 minutes and stirred under reduced pressure for 2 hours. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, then the obtained solid was washed with diethyl ether, and the residue was purified by column chromatography (silica gel, chloroform: ethyl acetate=10:0 to 8:2 (v/v)), yielding the target compound as a white solid: Yield 13%; 7.30-7.24 (m, 1H), 7.06-7.02 (m, 2H), 6.91-6.86 (m, 1H), 5.49 (s, 1H), 4.80 (d, 1H, J=6.6 Hz), 4.29 (dd, 1H, J=9.8, 4.4 Hz), 3.98-3.90 (m, 3H), 3.85-3.70 (m, 2H), 3.68-3.60 (m, 1H), 3.51-3.42 (m, 4H), 2.73 (br, 1H), 2.29 (br, 1H), 1.81-1.72 (m, 2H), 1.50-1.41 (m, 2H), 1.39-1.30 (m, 4H), 0.93-0.88 (m, 3H).

<Synthesis of Glucose Gelator from Diethyl Acetal Derivative>

In accordance with scheme 7 below, diethyl acetal derivatives were reacted with methyl α-D-glucopyranoside, yielding compounds [G3] and [G4] as glucose gelators.

Scheme 7

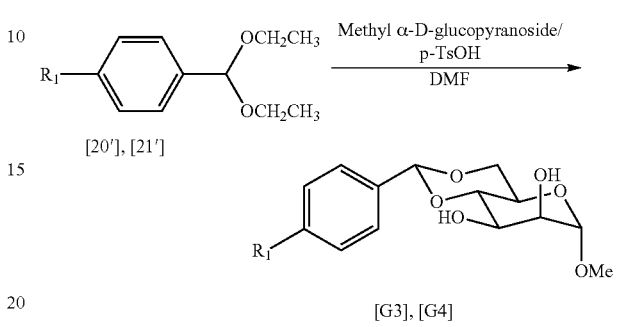

[20'], [G3] R$_1$ = CH$_3$(CH$_2$)$_3$O,
[21'], [G4] R$_1$ = CH$_3$(CH$_2$)$_4$O,

Synthesis of compound [G3]: Under a nitrogen atmosphere, to a solution of methyl α-D-glucopyranoside (2.5 g, 13 mmol) in DMF (6 mL), p-toluenesulfonic acid (46 mg, 0.3 mmol) was added, and the mixed solution was stirred at room temperature for 5 minutes. To the mixed solution, a solution of 4-butoxybenzaldehyde diethyl acetal [20'] (2.9 g, 12 mmol) in DMF (6 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diisopropyl ether, yielding the target compound as a white solid: Yield 85%.

Synthesis of compound [G4]: Under a nitrogen atmosphere, to a solution of methyl α-D-glucopyranoside (2.0 g, 10 mmol) in DMF (9 mL), p-toluenesulfonic acid (52 mg, 0.3 mmol) was added, and the mixed solution was stirred at room temperature for 5 minutes. To the mixed solution, a solution of 4-pentyloxybenzaldehyde diethyl acetal [21'] (2.5 g, 9 mmol) in DMF (5 mL) was added dropwise at room temperature. After the dropwise addition, the mixed solution was stirred at room temperature for 10 minutes and stirred under reduced pressure for 1 hour. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with diisopropyl ether, yielding the target compound as a white solid: Yield 72%.

[One-Step Synthesis of Glucose Gelator from Aromatic Aldehyde Compound]

Synthesis of Glucose Gelator Using Methyl-α-D-Glucopyranoside

In accordance with scheme 8 below, compounds [G3] and [013'] were synthesized as glucose gelators from aromatic aldehyde compounds in one step.

Scheme 8

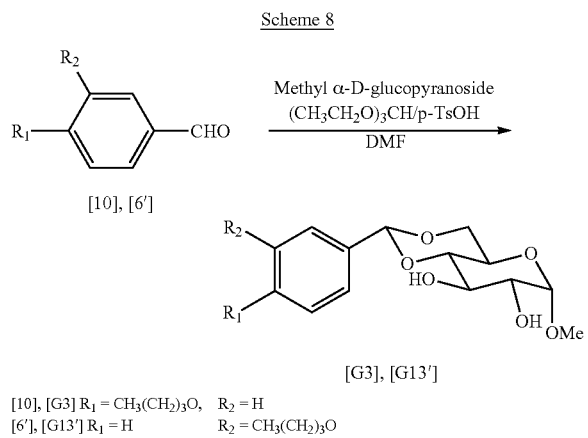

[10], [G3] R₁ = CH₃(CH₂)₃O, R₂ = H
[6'], [G13'] R₁ = H        R₂ = CH₃(CH₂)₃O

Synthesis of compound [03]: Under a nitrogen atmosphere, to a solution of methyl α-D-glucopyranoside (1.9 g, 10 mmol) in DMF (7 mL), 4-butoxybenzaldehyde [10] (1.8 g, 10 mmol) and p-toluenesulfonic acid (52 mg, 0.27 mmol) were added, and the mixed solution was stirred at room temperature for 10 minutes. To the mixed solution, triethyl orthoformate (1.5 g, 10 mmol) was added dropwise at room temperature. After the dropwise addition, the mixed solution was stirred at room temperature for 20 minutes and stirred under reduced pressure for 2 hours. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with hexane, yielding the target compound as a white solid: Yield 78%.

Synthesis of compound [G13']: Under a nitrogen atmosphere, to a solution of methyl α-D-glucopyranoside (3.9 g, 20 mmol) in DMF (13 mL), 3-butoxybenzaldehyde [G6'] (3.6 g, 20 mmol) and p-toluenesulfonic acid (92 mg, 0.5 mmol) were added, and the mixed solution was stirred at room temperature for 10 minutes. To the mixed solution, triethyl orthoformate (3.8 g, 26 mmol) was added dropwise at room temperature. After the dropwise addition, the mixed solution was stirred at room temperature for 20 minutes, then stirred under reduced pressure at room temperature for 1 hour, and stirred at 40° C. for 2 hours. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with hexane, yielding the target compound as a white solid: Yield 65%; $^1$H NMR (500 MHz, CDCl$_3$): δ 7.30-7.25 (m, 1H), 7.06-7.03 (m, 2H), 6.89 (d, 1H, J=9.2 Hz), 5.50 (s, 1H), 4.81 (d, 1H, J=3.8 Hz), 4.29 (q, 1H, J=4.8 Hz), 3.99-3.91 (m, 3H), 3.84-3.78 (m, 1H), 3.74 (t, 1H, J=10.3 Hz), 3.65 (t, 1H, J=9, 5 Hz), 3.52-3.42 (m, 4H), 2.63 (s, 1H), 121 (d, 1H, J=9.4 Hz), 1.79-1.72 (m, 2H), 1.53-1.44 (m, 2H), 0.97 (t, 3H, J=7.5 Hz).

<Synthesis of Glucose Gelator Using Ethyl α-D-Glucopyranoside>

In accordance with scheme 9 below, compound [G3'] was synthesized as a glucose gelator from an aromatic aldehyde compound in one step.

Scheme 9

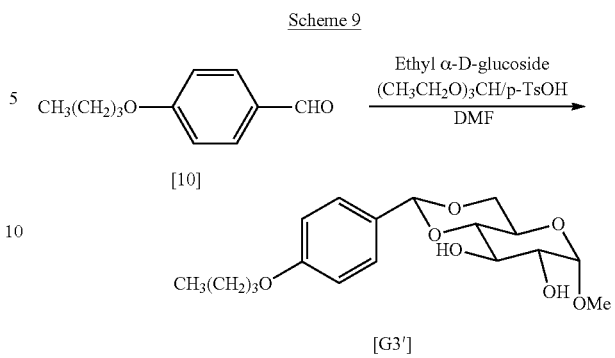

Synthesis of compound [G3']: Under a nitrogen atmosphere, to a solution of ethyl α-D-glucoside (1.1 g, 5 mmol) in DMF (3 mL), 4-butoxybenzaldehyde [G10] (0.9 g, 5 mmol) and p-toluenesulfonic acid (22 mg, 0.1 mmol) were added, and the mixed solution was stirred at room temperature for 10 minutes. To the mixed solution, triethyl orthoformate (0.8 g, 5 mmol) was added dropwise at room temperature. After the dropwise addition, the mixed solution was stirred at room temperature for 1 hour and stirred under reduced pressure at room temperature for 2 hours. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with hexane, yielding the target compound as a white solid: Yield 66%; $^1$H NMR (500 MHz, CDCl$_3$): δ 7.40 (d, 2H, J=8.5 Hz), 6.88 (d, 2H, J=8.8 Hz), 5.49 (s, 1H), 4.91 (d, 1H, J=4.1 Hz), 4.26 (q, 1H, J=4.8 Hz), 3.98-3.91 (m, 3H), 3.86-3.79 (m, 2H), 3.72 (t, 1H, J=10.3 Hz), 3.65-3.52 (m, 2H), 3.48 (t, 1H, J=9.5 Hz), 2.63 (s, 1H), 2.19 (d, 1H, J=10.1 Hz), 1.79-1.72 (m, 2H), 1.51-1.44 (m, 2H), 1.27 (t, 3H, 0.1=7.1 Hz), 0.97 (t, 3H, J=7.5 Hz).

<Synthesis of Glucose Gelator Using D(+)-Glucose>

In accordance with scheme 10 below, compound [G3"] was synthesized as a glucose gelator from an aromatic aldehyde compound in one step.

Scheme 10

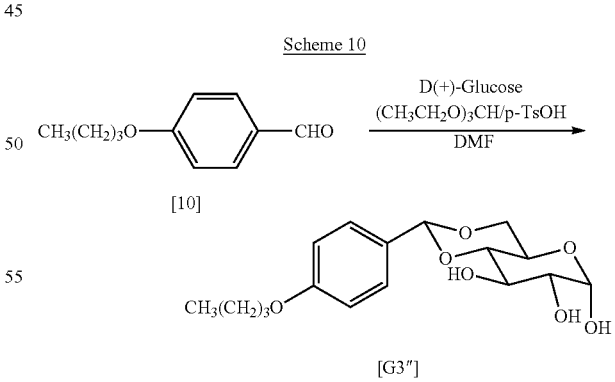

Synthesis of compound [G3"]: Under a nitrogen atmosphere, to a solution of D (+)-glucose (1.8 g, 10 mmol) in DMF (7 mL), 4-butoxybenzaldehyde [G10] (1.9 g, 10 mmol) and p-toluenesulfonic acid (54 mg, 0.3 mmol) were added, and the mixed solution was stirred at room temperature for 10 minutes. To the mixed solution, triethyl orthoformate (1.5 g, 10 mmol) was added dropwise at room temperature. After the dropwise addition, the mixed solution was stirred at room temperature for 20 minutes and stirred under reduced pressure at room temperature for 5 hours. To the reaction solution, a saturated aqueous sodium hydrogen carbonate solution was added, and the mixture was extracted with ethyl acetate. The extract was washed with a saturated salt solution and then was dried over anhydrous sodium sulfate. After filtration, the filtrate was concentrated under reduced pressure, and the obtained solid was washed with hexane. The product was purified by column chromatography (silica gel, chloroform: methanol=10:0 to 9:1 (v/v)), yielding a white solid.

Figure 2:
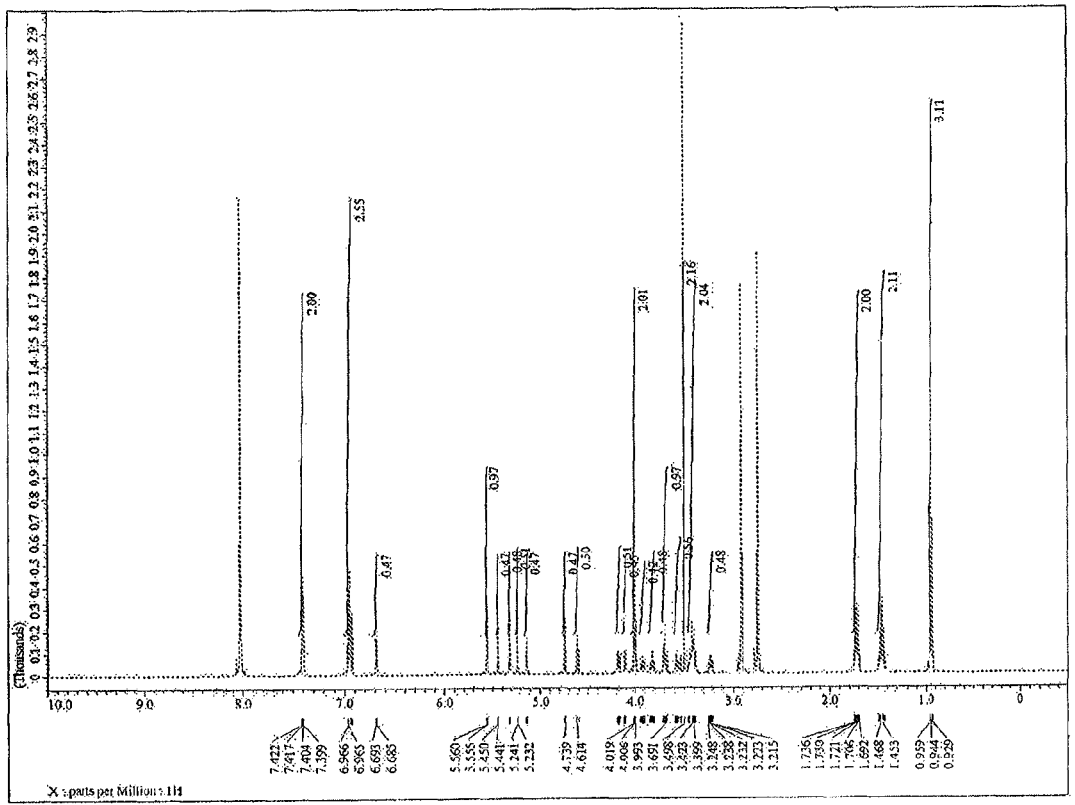
FIG. 2 is a view showing a $^1$H NMR (500 MHz, in deuterated DMF) spectrum of the purified compound [G3"] prepared in Examples.

An HPLC chart and $^1$H NMR (500 MHz) of the product after purification are shown in FIG. 1 and FIG. 2, respectively. The HPLC observation indicates two components (retention time: 2.16 minutes and 2.31 minutes (solvent: acetonitrile/water=50/50)), and the $^1$H NMR also suggests two components. However, LC-MS observation shows a molecule ion peak (EST-MS cald for $C_{17}H_{25}O_7$ [M+H]$^+$341. found 341) of the target compound. Consequently, the target compound was obtained as a mixture of α-form and β-form: Yield 32%.

Example 2 to Example 17

Gel Forming Ability of Gelator and Various Evaluations of Gel Obtained

Evaluation of the abilities of compounds M1 to M10, G1 to G9, and G11 to G13 synthesized in Example 1 as gelators to form gels (gel forming ability) from various solvents and various evaluations of gels obtained were carried out. At the same time, each gel forming ability was compared with those of compound A of methyl α-D-4,6-benzylidenemannose and compound B of methyl α-D-4,6-benzylideneglucose that are known substances (Non-Patent Document 1).

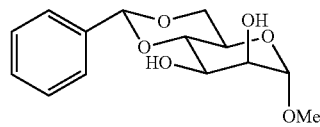

A

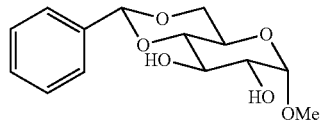

B

Example 2

Comparison of Gel Forming Ability with Known Substance

Gelation test was carried out as follows. Into a 4-mL screw tube, a gelator and various solvents were added, and the mixture was heated for 30 minutes to be dissolved under a heating condition as follows: at 90° C. for cyclohexane, acetonitrile, methanol, ethanol, and a mixed solvent of ethanol and water; at 100° C. for toluene, water, and a mixed solvent of DMSO and water; and at 120° C. for octane, SH245, olive oil, isopropyl myristate, ethylene glycol, and glycerol. The obtained solution was allowed to cool to room temperature and left for 1 hour, and the gel formation was observed. After the cooling, a state where the solution had no flowability and did not run off even when the sample tube was placed in reverse was determined as "gelated". The gelation test was carried out at gelator concentrations of 2.0, 1.0, 0.5, 0.25, and 0.1 wt %, and the minimum gelator concentration (wt %) required for the gelation was regarded as a minimum gelation concentration. Here, wt % representing the unit for concentration means wt/vol×100. The obtained results are shown in Table 1 and Table 2. The numeric characters in Tables are minimum gelation concentrations (wt %), the signs in Tables show states of the gels formed, where a transparent gel is represented as "G", a translucent gel is represented as "#G", a cloudy gel is represented as "*G", a crystallized gel is represented as "Cr", a partial gel is represented as "PG", and a sample failed to form a gel even at a gelator concentration of 2 wt % is represented as "–".

Table 1 shows the results of the gelation test of compounds M1 to M10 as mannose gelators and compound A, and Table 2 shows the results of the gelation test of compounds G3 and G8 as glucose gelators and compound B.

TABLE 1

Gelation test results of mannose gelators (M1 to M10) and a known substance (A)

| Solvent | A | M1 | M2 | M3 | M4 | M5 | M6 | M7 | M8 | M9 | M10 |
|---|---|---|---|---|---|---|---|---|---|---|---|
| Octane | 0.25 | 0.1 | 0.05 | 0.1 | 0.1 | 0.1 | 0.25 | — | 0.1 | — | 0.05 |
|  | *G | G | G | G | G | G | G |  | G |  | G |
| Cyclohexane | 0.5* | 0.25 | 0.05 | 0.05 | 0.1 | 0.25 | 0.1 | — | 0.5 | — | 0.25 |
|  | G | G | G | G | G | G | G |  | G |  | G |
| Toluene | 0.5 | 0.5 | 0.5 | 1 | 1 | 2 | 2 | — | 0.5 | — | — |
|  | *G | G | G | G | G | G | G |  | G |  |  |
| SH245 | 0.025 | 0.05 | 0.05 | 0.05 | 0.25 | 0.25 | 0.5 | — | 0.05 | — | 0.1 |
|  | G | G | G | G | G | G | G |  | G |  | G |
| Olive oil | 1 | 0.5 | 0.5 | 1 | 1 | 1 | 1 | — | 0.5 | — | — |
|  | #G | G | G | G | G | G | G |  | G |  |  |
| Isopropyl myristate | 1 | 0.5 | 0.5 | 1 | 1 | 1 | 1 | — | 0.5 | — | — |
|  | *G | G | G | G | G | G | G |  | G |  |  |
| Ethylene glycol | — | — | 2 | 2 | 1 | 0.5 | 0.25 | — | — | — | — |
|  |  |  | #G | #G | #G | #G | #G |  |  |  |  |
| Glycerol | — | — | 2 | — | — | — | — | — | 2 | — | — |
|  |  |  | #G |  |  |  |  |  | #G |  |  |

TABLE 1-continued

Gelation test results of mannose gelators (M1 to M10) and a known substance (A)

| Solvent | A | M1 | M2 | M3 | M4 | M5 | M6 | M7 | M8 | M9 | M10 |
|---------|---|----|----|----|----|----|----|----|----|----|----|
| Water | 3 *G | — | 0.1 *G | — | — | — | — | 2 *G | 0.1 #G | — | — |

*The numerical values in Table are minimum concentrations (wt %) of the gelators (compounds) required for the gelation of respective solvents.
*G: transparent gel; #G: translucent gel; *G: cloudy gel; Cr: crystallized gel; PG: partial gel; —: failed to form a gel

TABLE 2

Gelation test results of glucose gelators (G3 and G8) and known substance (B)

| Solvent | B | G3 | G8 |
|---------|---|----|----|
| Toluene | 1 Cr | 1 G | 1 G |
| SH245 | 0.5 *G | 0.25 G | 0.1 PG |
| Acetonitrile | — | — | 2 #G |
| Methanol | — | — | 2 #G |
| Ethanol | — | — | 2 G |
| Ethylene glycol | — | 2 *G | 0.05 G |
| Water | 2 *G | 0.1 G | — |
| DMSO/water (75/25) | — | — | 0.1 G |
| DMSO/water (50/50) | — | 1 #G | 0.25 #G |
| DMSO/water (25/75) | — | 0.25 #G | — |
| Ethanol/water (75/25) | — | — | 0.5 #G |
| Ethanol/water (50/50) | — | — | 0.05 #G |
| Ethanol/water (25/75) | — | 0.25 #G | 1 *G |

*The numerical values in Table are minimum concentrations (wt %) of the gelators (compounds) required for the gelation of respective solvents.
*G: transparent gel;
G: translucent gel;
*G: cloudy gel;
Cr: crystallized gel;
PG: partial gel;
—: failed to form a gel Table 1 and Table 2 show that the gelators of the present invention can form highly transparent gels from various solvents as compared with the gelator including compound A or compound B as known substances and have low minimum gelation concentrations. Interestingly, the results show that the gelator of the present invention is a compound prepared by introducing a hydrocarbon group as a hydrophobic functional group to compound A or compound B as a known substance, but has high ability to form a gel from polar solvents (water, ethanol, and ethylene glycol) having high polarity while maintaining the ability to form a gel from nonpolar solvents (octane, toluene, and SH245). In particular, G3 as the glucose gelator formed a comparatively, highly transparent gel from water.

Next, the gelation test of mannose gelators M2, M4, and M6 synthesized in Example 1 and compound A as a known substance was carried out by using a mixed solvent of ethanol and water and a mixed solvent of DMSO and water in accordance with the procedure described above, and the gel forming abilities of the gelators were evaluated. The obtained results are shown in Table 3 and Table 4.

TABLE 3

Results of gelation test of a mixed solvent and of ethanol and water

| | Ethanol/water (vol/vol) | | | | |
|---|---|---|---|---|---|
| | 100/0 | 75/25 | 50/50 | 25/75 | 0/100 |
| A | — | — | — | — | — |
| M2 | — | — | 1 *G | 0.1 #G | 0.1 *G |
| M4 | — | — | 0.5 *G | 0.2 #G | — |
| M6 | — | 1 G | 1 *G | — | — |

*The numerical values in Table are minimum concentrations (wt %) of the gelators (compounds) required for the gelation of respective mixed solvents.
*G: transparent gel;
G: translucent gel;
*G: cloudy gel;
Cr: crystallized gel;
PG: partial gel;
—: failed to form a gel

TABLE 4

Results of gelation test of a mixed solvent of DMSO and water

| | DMSO/water (vol/vol) | | | | |
|---|---|---|---|---|---|
| | 100/0 | 75/25 | 50/50 | 25/75 | 0/100 |
| A | — | — | — | — | — |
| M2 | — | — | 0.25 #G | 0.1 #G | 0.1 *G |
| M4 | — | 2 G | 2 G | 1 #G | — |
| M6 | — | 0.5 #G | 1 #G | — | — |

*The numerical values in Table are minimum concentrations (wt %) of the gelators (compounds) required for the gelation of respective mixed solvents.
*G: transparent gel;
G: translucent gel;
*G: cloudy gel;
Cr: crystallized gel;
PG: partial gel;
—: failed to form a gel As shown in Table 3 and Table 4, neither the mixed solvent of ethanol and water nor the mixed solvent of DMSO and water formed a gel with compound A as a known substance. In contrast, the results obtained reveal that mannose gelators M2, M4, and M6 synthesized in Example 1 can form a gel from the mixed solvent of ethanol and water and from the mixed solvent of DMSO and water. The results also reveal that a gelator compound having a shorter alkyl chain as the hydrocarbon group bonded to the benzene ring can form a gel from a mixed solvent containing water at a higher ratio.

Example 3

Thixotropic Property Test

The thixotropic properties of various gels formed with mannose gelators were evaluated. The thixotropic property test was carried out as follows. A gel was prepared at a minimum gelation concentration in the same manner as in Example 2. The gel was shook with a vortex mixer to be disintegrated until a sol was formed, and was left at room temperature for 1 hour. After 1 hour, the sample tube containing the solution was placed in reverse, and a state where the solution did not run off was determined as "having thixotropic properties". Table 5 shows the obtained results. In Table, a sample determined to have thixotropic properties is represented as "○", a sample determined to have no thixotropic properties is represented as "x", and a sample failed to form a gel is represented as "–".

TABLE 5

Thixotropic property evaluation of mannose gelators

|  | A | M1 | M2 | M3 | M4 | M5 | M6 | M8 | M10 |
|---|---|---|---|---|---|---|---|---|---|
| Toluene | X | ○ | ○ | ○ | ○ | ○ | ○ | ○ | — |
| SH245 | X | X | X | X | X | ○ | ○ | X | X |

As shown in Table 5, the results obtained reveal that the gelators having a hydrocarbon group of the present invention form a gel having thixotropic properties, as compared with known compound A.

Example 4

Storage Stability

Gels of SH245 containing 0.05 wt % of mannose gelators M1 and M3 produced in Example 1 and compound A as a known substance were left at room temperature for 7 days, and the stability of each gel was evaluated. The obtained results are shown in FIG. 3.

Figure 3:
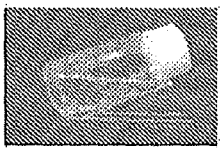
FIG. 3 is a view showing stabilities of SH245 gels that were prepared form SH245 with mannose gelators M1 and M3 and compound A as a known substance (each 0.05 wt %) and left at room temperature for 7 days.
Figure 3:
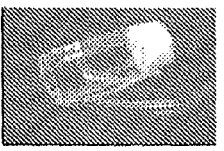
Figure 3:
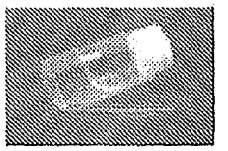

As shown in FIG. 3, the results obtained reveal that the gelator of the present invention released a smaller amount of liquid and thus had excellent storage stability as compared with the gelator including compound A as a known substance. The results obtained also reveal that a gelator compound having a longer alkyl chain as the hydrocarbon group bonded to the benzene ring released a smaller amount of liquid, and this suggests that the alkyl chain length greatly affects the storage stability of the gel.

Example 5

Gelation Test of Glucose Gelator

As shown in Example 2 to Example 4, the result obtained reveal that each of the mannose gelators and the glucose gelators as the gelators of the present invention has good gel forming ability as compared with compound A and compound B as known substances. The results obtained also suggest that the introduction of an alkyl chain allows the gelator to form a gel having excellent thixotropic properties and storage stability.

Considering these results, the glucose gelators, which were suggested to have relatively high ability to form a gel from polar solvents, were subjected to gelation test by using oils (isopropyl myristate, olive oil, and SH245) that are frequently used in cosmetics and by using an aqueous solution containing alcohol (ethanol). The results are shown in Table 6. The gelation test was carried out under the same conditions as in Example 2.

TABLE 6

Gelation test results of glucose gelators

| | Aqueous solution containing alcohol | | | | | Oil | | |
|---|---|---|---|---|---|---|---|---|
| | Ethanol/water (vol/vol) | | | | | Isopropyl myristate | Olive oil | SH245 |
| | 100/0 | 75/25 | 50/50 | 25/75 | 0/100 | | | |
| G1 | 2 *G | — | — | 2 #G | 1 #G | 0.5 PG | 0.5 G | — |
| G2 | — | — | — | 0.5 #G | 0.25 #G | 0.5 #G | 0.5 G | 2 PG |
| G3 | — | — | — | 0.25 #G | 0.1 G | 0.5 PG | 1 #G | 0.25 G |
| G4 | — | — | 2 #G | 0.1 G | 0.1 PG | 0.5 #G | 1 #G | 0.25 G |
| G5 | — | — | 1 PG | 0.1 #G | — | 1 #G | 1 #G | 0.25 G |
| G6 | — | 2 #G | 0.25 G | 0.1 G | — | 1 PG | 1 #G | 0.1 PG |
| G7 | — | 1 #G | 0.1 #G | 0.1 PG | — | 1 PG | 1 #G | 0.1 PG |
| G8 | 2 G | 0.5 #G | 0.05 #G | 1 *G | — | 1 #G | 1 #G | 0.1 PG |
| G9 | — | — | — | 0.5 #G | 0.25 #G | 1 #G | 1 #G | — |
| G11 | 2 *G | 2 *G | 2 *G | 0.5 *G | — | 0.5 #G | 0.5 #G | — |
| G12 | — | — | 2 *G | 2 *G | — | 1 #G | 2 #G | 0.25 #G |
| G13 | — | — | 1 *G | 0.1 #G | 0.5 #G | — | 2 #G | 0.25 #G |
| G13' | — | — | — | 0.5 *G | 0.25 *G | 1 G | 2 #G | 0.1 G |
| G3' | — | — | 2 *G | 0.25 *G | 0.1 PG | 1 #G | 1 G | 0.25 #G |
| G3" | — | — | — | 2 *G | 1 *G | 2 *PG | — | — |

*The numerical values in Table are minimum concentrations (wt %) of the gelators (compounds) required for the gelation of respective solvents.

*G: transparent gel; #G: translucent gel; *G: cloudy gel; Cr: crystallized gel; PG: partial gel; *PG: partially cloudy gel; —: failed to form a gel As shown in Table 6, almost all the gelators formed gels from the oils used in the test. In particular, the results obtained reveal that G1 to G4, G9, and G13 formed comparatively highly transparent gels from water. The test results of G1 to G8 where ethanol was added reveal that a gelator compound having a longer alkyl chain as the hydrocarbon group bonded to the benzene ring tends to be able to form a gel even when an aqueous solution contains the alcohol at a higher ratio.

Example 6

Thixotropic Property Test of Gel from Aqueous Solution Containing Alcohol

The test where alcohol was added in Example 5 has revealed the amount of alcohol in an aqueous solution that can form a gel with each glucose gelator. The thixotropic property test of the gels formed from an aqueous solution containing alcohol was then carried out in the same manner as in Example 3. The thixotropic property test was carried out as follows. A gel was prepared in the same manner as in Example 5, and the thixotropic property test was carried out in the same manner as in Example 3. Here, the gelator was first prepared at the minimum gelation concentration, and the concentration gradually increased until the resulting gel exhibited thixotropic properties while the expression of the thixotropic properties was observed. The results are shown in Table 7. In Table, the numeric character (lower line) in each frame is the concentration (wt %) of the gelator where thixotropic properties were observed, and the numeric character and symbol in parentheses (upper line) are a minimum gelation concentration and a gel state shown in Example 5. The results of compound B as a known substance are the same as those shown in Example 2. The concentration of the gelator was set to 0.1, 0.25, 0.5, 1.0, and 2.0 wt %. A gelator failed to exhibit the thixotropic properties within the set concentrations is represented as "x".

TABLE 7

Thixotropic property evaluation of gel formed from aqueous solution containing alcohol

| | Aqueous solution containing alcohol Ethanol/water (vol/vol) | | | | |
|---|---|---|---|---|---|
| | 100/0 | 75/25 | 50/50 | 25/75 | 0/100 |
| B | (—) | (—) | (—) | (—) | (2 *G) x |
| G1 | (2 *G) x | (—) | (—) | (2 #G) x | (1 #G) x |
| G3 | (—) | (—) | (—) | (0.25 #G) 0.25 | (0.1 G) 1 |
| G5 | (—) | (—) | (1 PG) 1 | (0.1 #G) 0.25 | (—) |
| G6 | (—) | (2 #G) 2 | (0.25 G) 0.25 | (0.1 G) 0.25 | (—) |
| G7 | (—) | (1 #G) 1 | (0.1 #G) 0.5 | (0.1 PG) 2 | (—) |
| G8 | (2 G) 2 | (0.5 #G) 1 | (0.05 #G) 0.25 | (1 *G) x | (—) |

*The numerical values in parentheses are minimum concentrations (wt %) of the gelators (compounds) required for the gelation.
*G: transparent gel;
G: translucent gel;
*G: cloudy gel;
Cr: crystallized gel;
PG: partial gel;
—: failed to form a gel
* The numerical values in lower lines are concentrations (wt %) of gelators (compounds) exhibiting the thixotropic properties.
(x: Failed to exhibit thixotropic properties)

As shown in Table 7, as a gelator compound had a longer alkyl chain as the hydrocarbon group bonded to the benzene ring, the expression of thixotropic properties was observed. Compound B as a known compound was observed to express no thixotropic properties. Specifically, the results obtained reveal that the gels that form transparent gels or translucent gels represented as G or #G tend to achieve thixotropic properties at around the minimum gelation concentration.

Example 7

Additive Addition Test

Cosmetics and quasi-drugs commonly contain preservatives and surfactants. The ability of the gelator of the present invention to form a gel was studied when a preservative or a surfactant was added.

<Preservative Addition Test>

Preservative addition test was carried out as follows. A preservative was dissolved in water so as to give a predetermined concentration to prepare an aqueous preservative solution. Into a 4-mL screw tube, a gelator (glucose gelator G3) was added so as to give a predetermined concentration, the aqueous preservative solution prepared above was added, and the mixture was heated at 100° C. for 30 minutes and dissolved. The obtained solution was allowed to cool to room temperature and left for 1 hour. The screw tube was placed in reverse, and the gel formation was observed. The results are shown in Table 8. The preservatives used were methylparaben alone, phenoxyethanol alone, and a mixture of them.

TABLE 8

Preservative addition test

| | G3 concentration 0.1 wt % | | |
|---|---|---|---|
| Preservative | Methylparaben | Phenoxyethanol | Methylparaben + phenoxyethanol |
| Preservative concentration | 0.2 wt % | 0.5 wt % | 0.2 wt % + 0.5 wt % |
| Result | Gelated | Gelated | Gelated |

As shown in Table 8, the results obtained reveal that the gelator of the present invention can form a gel even when the preservative is added.

<Surfactant Addition Test>

Surfactant addition test was carried out as follows. A surfactant was dissolved in water so as to give a predetermined concentration to prepare an aqueous surfactant solution. Into a 4-mL screw tube, a gelator (glucose gelator G3) was added so as to give a predetermined concentration, then the aqueous surfactant solution prepared above was added, and the mixture was heated at 100° C. for 30 minutes and dissolved. The obtained solution was allowed to cool to room temperature and left for 1 hour. The screw tube was placed in reverse, and the gel formation was observed. The results are shown in Table 9. The surfactants used were polyoxyethylene sorbitan monolaurate (Tween 20) as a nonionic surfactant, sodium dodecyl sulfate (SDS) as an anionic surfactant, stearyltrimethylammonium bromide (STAB) as a cationic surfactant, and 3-[(3-cholamidopropyl)dimethylammonio]propanesulfonate (CHAPS) as an amphoteric surfactant.

TABLE 9

Surfactant addition test

| | G3 concentration 2.0 wt % | | | |
|---|---|---|---|---|
| Surfactant | Tween 20 | SDS | STAB | CHAPS |
| Surfactant concentration | | 2.5 wt % | | |
| Result | Gelated | Gelated | Gelated | Gelated |

As shown in Table 9, the results obtained reveal that the gelator of the present invention can form a gel even when the surfactant is added.

Example 8

Water/Oil Dispersion Test with Glucose Gelator

A surfactant is commonly used in order to uniformly disperse an oil and water and to stabilize the dispersion in creams and cleansing creams of cosmetics. However, the amount of the surfactant is required to be reduced due to skin irritation and rough skin.

The results obtained in Example 7 reveal that the gelator of the present invention forms a good gel even when a surfactant is added. As shown in Example 2 and Example 5, the results obtained reveal that the gelator of the present invention, specifically, glucose gelators 01 to G4 form a gel from both water and oil solvents. The results suggest that the gelator of the present invention can uniformly disperse water and oil and can stabilize the dispersion without any surfactant. In Example 8, a water/oil dispersion test was thus carried out to determine whether the gelator of the present invention can uniformly disperse both the solvents of water and an oil.

The water/oil dispersion test was carried out as follows. Into a 4-mL screw tube, a gelator (glucose gelator G4 or G5) and various solvents were added so as to give a predetermined concentration, and the mixture was heated at 100° C. for 30 minutes and dissolved. The mixture was then sheared with a vortex mixer for 2 minutes and then was left at room temperature for 1 hour, and the dispersion state was observed. After the cooling, a state where the solution had no flowability and did not run off even when the sample tube was placed in reverse, and water and oil were uniformly dispersed was determined as "water/oil dispersion gel". At the time, a minimum concentration (wt %) of the gelator required for forming the water/oil dispersion gel is regarded as a minimum gelation concentration. The obtained results are shown in Table 10. In Table, the numeric characters are minimum gelation concentrations, a water/oil dispersion gel is represented as "G", a water/oil dispersion having flowability is represented as "W-sol", and a partial gel is represented as "PG".

For the water/oil dispersion test, G4 having the ability to form a gel from both water and oils and G5 having the ability to form a gel from oils alone were used. The concentrations of these gelators were 2.0, 1.0, 0.5, 0.25, and 0.1 wt %.

TABLE 10

Water/oil dispersion test with glucose gelator

| | | G4 | | G5 | |
|---|---|---|---|---|---|
| Squalane/water (vol/vol) | 7/3 | | W-sol | | W-sol |
| | 5/5 | 0.1 | G | | W-sol |
| | 3/7 | | PG | 0.25 | G |
| SH245/water (vol/vol) | 7/3 | 0.5 | G | 2.0 | G |
| | 5/5 | 0.25 | G | 2.0 | G |
| | 3/7 | 0.25 | G | 1.0 | G |
| Isopropyl myristate/water (vol/vol) | 7/3 | 1.0 | G | 1.0 | G |
| | 5/5 | 1.0 | G | 1.0 | G |
| | 3/7 | 1.0 | G | | PG |
| Olive oil/water (vol/vol) | 7/3 | 0.25 | G | 0.25 | G |
| | 5/5 | 0.25 | G | 1.0 | G |
| | 3/7 | 0.25 | G | | PG |

*The numerical values are minimum concentrations (wt %) of gelators (compounds) required for forming a water/oil dispersion gel.
*G: forming a water/oil dispersion gel;
PG: partial gel;
W-sol: a water/oil dispersion having flowability As shown in Table 10, the results obtained reveal that each of G4 and G5 formed a water/oil dispersion gel. In particular, the results obtained reveal that G4 that can form a gel from both water and oils has a lower minimum gelation concentration and can form the dispersion of water and oil in a wider range of combination ratio as compared with G5 that forms a gel from oils alone. Interestingly, the results reveal that in the systems represented by the water/oil dispersion gels (G) and W-sol, the water and the oil were not separated, and the shape (gel or Plowable shape) was able to be maintained for 4 months at room temperature.

Figure 4:
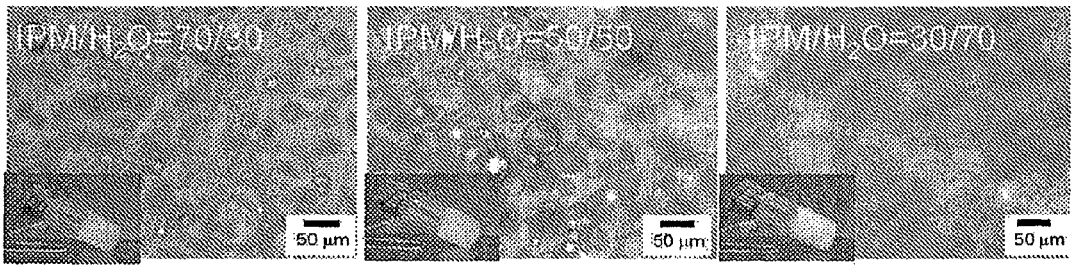
FIG. 4 is a view showing micrographs of water/oil dispersion gels from isopropyl myristate (IPM) and water with glucose gelator G4 (1 wt %).

FIG. 4 shows the observation results of the water/oil dispersion gels from isopropyl myristate (IPM) and water with G4 as a gelator, under an optical microscope. The droplets observed under an optical microscope had a size of about 10 to 50 µm.

Figure 5:
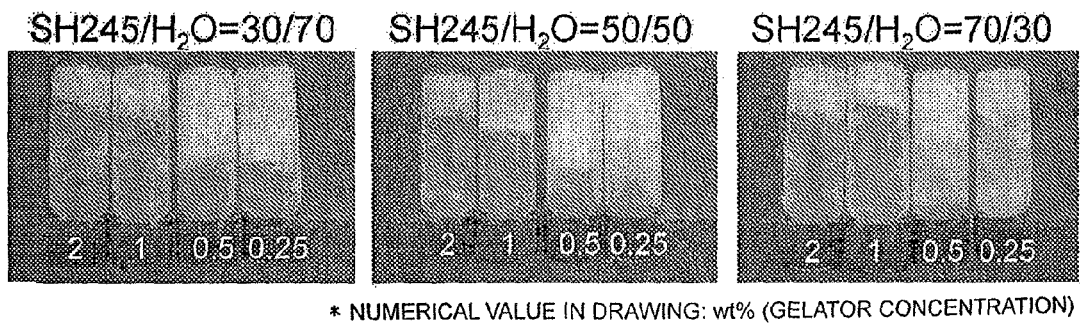
FIG. 5 is a view showing the appearances of water/oil dispersion gels from SH245 and water with glucose gelator G3 (0.25 to 1 wt %).
Figure 6:
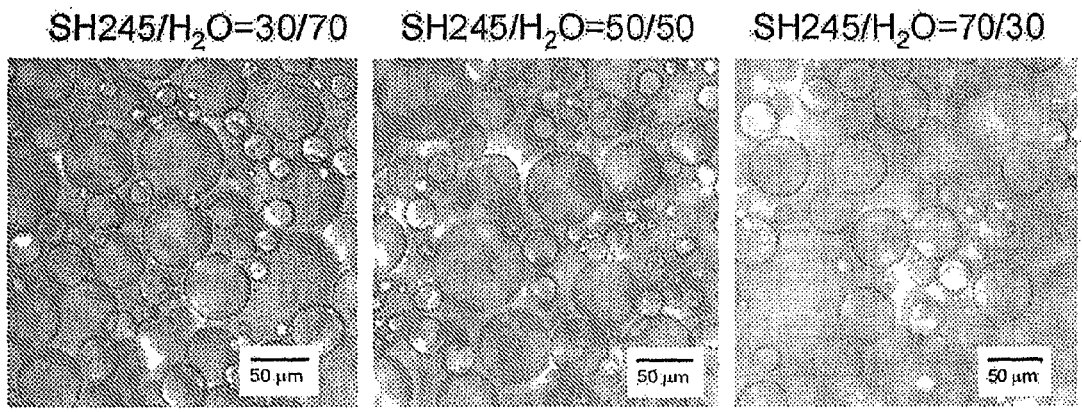
FIG. 6 is a view showing confocal laser scanning micrographs of water/oil dispersion gels from SH245 and water with glucose gelator G3 (0.25 wt %) (stirring means: vortex mixer).

In the same manner as for G4, G3 that can form a gel from both water and oil was subjected to the water/oil dispersion test using SH245 as the oil in the same conditions. FIG. 5 shows the appearances of the obtained water/oil dispersion gels. FIG. 6 shows the observation results of the water/oil dispersion gels under a confocal laser scanning microscope.

As shown in FIG. 5, as with G4, the results obtained reveal that G3 has a low minimum gelation concentration, can form a dispersion of water and the oil in a wide range of combination ratio, and can form a good water/oil dispersion gel. From the results of the observation under a confocal laser scanning microscope shown in FIG. 6, the droplets observed have a comparatively uniform size of about 10 to 50 µm.

Example 9

Water/Oil Dispersion Test with Homogenizer

In the water/oil dispersion test in Example 8, the gelator was dissolved in a solvent by heating, and then the solution was stirred with a vortex mixer. In the example, the water/oil dispersion test was carried out by using a homogenizer that is a stirring means having higher shear strength. By applying high shear strength with a homogenizer, formed droplets should have a smaller size.

Figure 7:
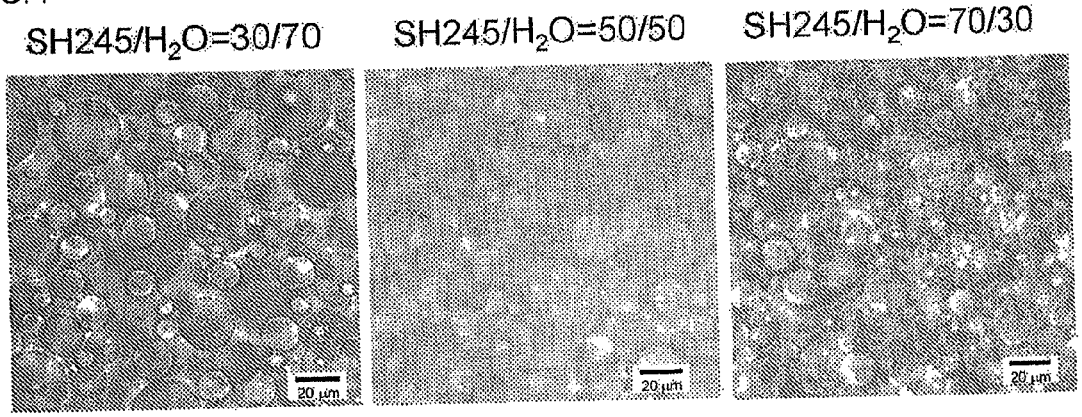
FIG. 7 is a view showing confocal laser scanning micrographs of water/oil dispersion gels from SH245 and water with glucose gelator G3 (0.25 wt %) (stirring means: homogenizer).

The water/oil dispersion test with a homogenizer was carried out as follows. Into a test tube, glucose gelator G3 (0.25 wt %) and a solvent (mixed solvent of SH245 and water: 30/70 to 70/30 (vol/vol)) were added, and the mixture was heated in an air bath at 100° C. for 30 minutes and dissolved. The solution was then sheared with a homogenizer for 5 minutes, and left at room temperature for 1 hour. The dispersion state was observed under a confocal laser scanning microscope. FIG. 7 shows the results.

As with the case using a vortex mixer, a uniform water/oil dispersion gel was formed by stirring with a homogenizer. The observation under a confocal laser scanning microscope reveal that the droplets formed with a homogenizer had a maximum size of about 30 μM (FIG. 7), which was relatively small as compared with the size (10 to 50 μm: FIG. 6) of the droplets formed with a vortex mixer. In other words, the results obtained suggest that by controlling the shear velocity after the gelator is heated and dissolved, the droplet diameter of the water/oil dispersion obtained can be controlled.

Example 10

Premix Test

The gelation test and the water/oil dispersion test in Example 2 to Example 9 were carried out by adding the gelator (compound) powder to various solvents and then heating and dissolving the mixture. The method is not a general-purpose method because it takes much time to dissolve the gelator powder in various solvents, and the time for dissolution varies with respective solvents. If a dispersion liquid in which the powder gelator is dissolved at high concentration is prepared in advance, and the addition of the dispersion liquid to various solvents allows speedy preparation of a gel or a water/oil dispersion gel, such a method would be speedy and simple in terms of the process for preparing a gel. The method of adding a high concentration dispersion liquid of the gelator to various solvents later and forming a gel or a water/oil dispersion gel in this manner is defined as "premix" in the present specification. In order to carry out premix test to determine whether the gelator of the present invention can be applied to the premix, a dispersion liquid in which the gelator can be dissolved at high concentration was studied.

<Study of Solvent for Dispersion Liquid for Premix>

Solvents used in a dispersion liquid were studied as follows. The gelator (glucose gelator G4) was added to various solvents so as to give a predetermined concentration (10 wt %), and the mixture was heated in an air bath at 80 to 100° C. for 30 minutes. The dissolution state of the gelator was observed, and the mixture was allowed to cool for 1 hour to room temperature. In order to determine whether the mixture can be used as a dispersion liquid for premix, redissolution test was carried out at 80° C. Solvents used in the dispersion liquids were alcoholic solvents of ethanol (EtOH), propylene glycol (PG), butylene glycol (BG), pentylene glycol (PenG), and glycerin (Gly). The results are shown in Table 11.

As shown in Table 11, as for the dispersion liquids prepared by adding U4 at a concentration of 10 wt % to various alcoholic solvents, it was ascertained that the dispersion liquids in ethanol, propylene glycol, butylene glycol, and pentylene glycol were uniformly dissolved on heating and were redissolved at 80° C. after cooling. In contrast, the dispersion liquid in glycerin was ascertained to remain a residue both on heating and on reheating, and this indicated insufficient solubility of a 10 wt % dispersion liquid of G4. The glycerin was thus determined to be unsuitable for a dispersion liquid for premix.

From these results, the propylene glycol that was able to redissolve the gelator was selected as the solvent for a dispersion liquid, and the premix test was carried out in accordance with the procedure below.

<Premix Test Using Dispersion Liquid>

The premix test was carried out as follows. First, into a screw tube, isopropyl myristate (21 g) was added and heated at 80° C. Into the screw tube, a 10 wt % dispersion liquid of G4 in propylene glycol (6.6 g) heated at 80° C. was added and made into a homogeneous solution, and then water (9 g) heated at 70° C. was added. The mixture was stirred with a homogenizer for 10 minutes, thus yielding a water/isopropyl myristate dispersion gel.

Figure 8:
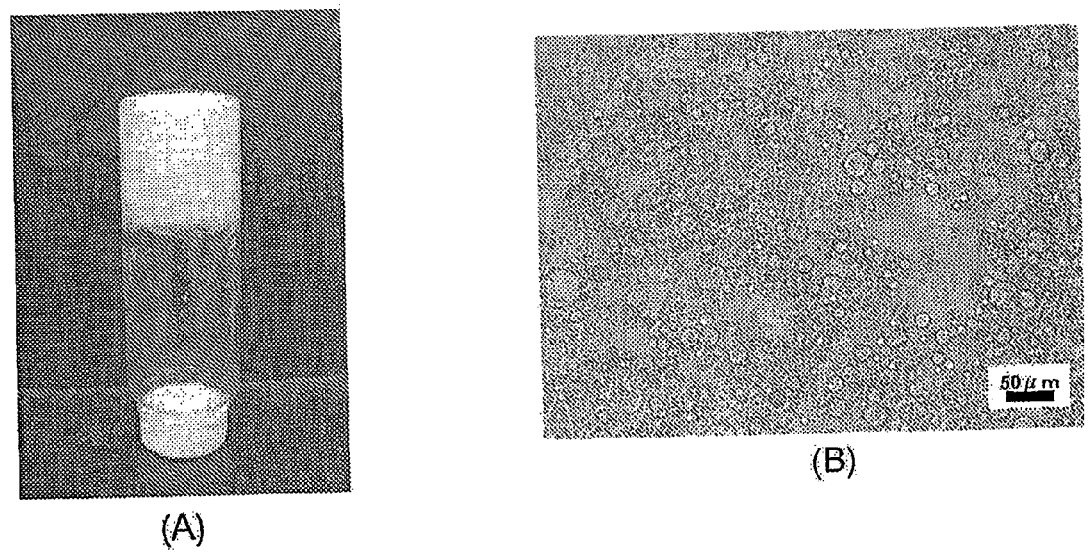
FIG. 8 are views showing the appearance (FIG. 8A) and a micrograph (FIG. 8B) of a gel prepared with a premix containing glucose gelator G4.

The final composition after the premix test was shown in Table 12. FIG. 8 show the appearance of the water/isopropyl myristate dispersion gel (FIG. 8A) and the result of microscope observation (FIG. 8B).

TABLE 12

| Final composition of gel after premix test | | |
|---|---|---|
| | Mass/g | % by mass |
| Isopropyl myristate | 21.0 | 57.4 |
| Water | 9.00 | 24.6 |
| Propylene glycol | 5.94 | 16.2 |
| Gelator G4 | 0.66 | 1.8 |
| Total amount | 36.6 | 100 |

As shown in FIG. 8, the results obtained reveal that a good water/oil dispersion gel is also formed by the premix method (FIG. 8A). As shown in the microscope observation (FIG. 8B), the results obtained reveal that the droplets have substantially the same size (a maximum size of about 30 μm) as that prepared from the powder.

TABLE 11

| Results of study for G4 dispersion liquid | | | | | |
|---|---|---|---|---|---|
| | EtOH | PG | BG | PenG | Gly |
| Gelator concentration/wt % | | | 10 | | |
| Heating temperature/° C. | 80 | 100 | 100 | 100 | 100 |
| On heating | Soluble | Soluble | Soluble | Soluble | Insoluble |
| After cooling | Opaque gel | Translucent gel | Translucent gel | Transparent gel | Opaque gel |
| On reheating at 80° C. | Soluble | Soluble | Soluble | Soluble | Insoluble |

PG: propylene glycol;
BG: butylene glycol;
PenG: pentylene glycol;
Gly: glycerin

Example 11

Gel Release Test

The gel prepared with the gelator of the present invention has a solidity sufficient for self-standing, but is very fragile against shear to exhibit liquidity, and solidifies immediately after the shearing. Due to these features, a prepared gel can be easily released from a container, can be easily cut with a sharp knife, and can maintain a gel shape without causing syneresis after the cutting.

<Gel Release Test Using Mannose Gelator (M3)>

Figure 9:
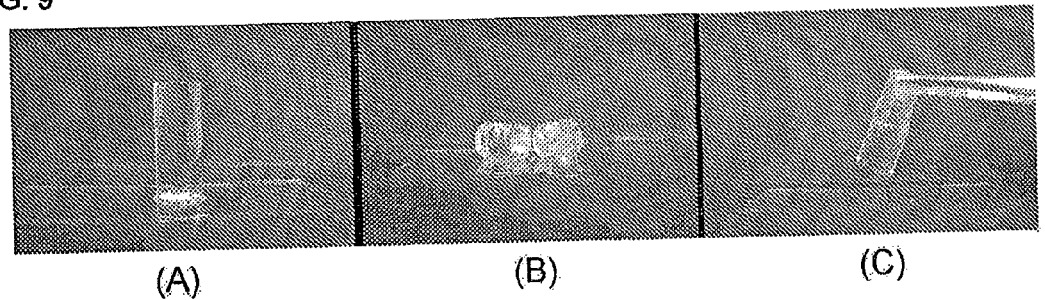
FIG. 9 are views showing the appearances of a squalene gel that was prepared with mannose gelator M3 (0.5 wt %) and released from a sample tube.

The gel release test using mannose gelator (M3) was carried out as follows: Into a sample tube, M3 and squalene (2.5 mL) were added so as to give a concentration of 0.5 wt %, the mixture was heated at 130° C. for 30 minutes and dissolved, and the solution was allowed to cool to room temperature for 1 hour, thus yielding a gel. The gel was then slowly released with a spatula. FIG. 9 show photographs of the appearance of the gel released from the sample tube. FIG. 9A is a photograph of the gel immediately after the release; FIG. 9B is a photograph of gels prepared by cutting the released gel with a cover glass (a thickness of 0.12 to 0.17 mm); and FIG. 9C is a photograph of a stacked gel by joining the cut sections of the cut gel to each other.

As shown in FIG. 9, the results obtained reveal that the released gel is a self-standing gel (having self-standing properties), can form a gel shape without causing syneresis after shearing, and can be rebonded by stacking cut sections with each other, that is, can have self-repairing properties.

<Gel Release Test Using Glucose Gelator (G4)>

In the same manner as for mannose gelator (M3), the gel release test was carried out by using G4 as the glucose gelator. Into a sample tube, glucose gelator (G4) and various solvents were added so as to give a predetermined concentration, and the mixture was heated at 120 to 130° C. for 30 minutes and dissolved. The solution (about 2 mL) was then poured into a standing cylindrical tube and was allowed to cool to room temperature for 1 hour, thus yielding a gel. The gel was slowly pushed out of the cylindrical tube and subjected to the gel release test. The results are shown in Table 13. The symbols in Table, a gel capable of maintaining a gel shape after the release was determined as "○", a little loose gel was determined as "Δ", and a gel that failed to maintain the shape was determined as "x". The oblique lines indicate not tested.

TABLE 13

Release test results of G4 gels

| | | Solvent | | | |
|---|---|---|---|---|---|
| | SH245 | Olive oil | Isopropyl myristate | Squalane | Squalene |
| Heating temperature/° C. | 130 | 130 | 120 | 130 | 130 |
| G4 wt % 0.5 | Δ | / | X | Δ | / |
| 1.0 | ○ | X | Δ | ○ | X |
| 2.0 | ○ | Δ | ○ | ○ | ○ |
| 3.0 | / | ○ | / | / | / |

○: A gel shape was maintained after release;
Δ: a gel shape was a little loosened after release;
X: a gel shape was failed to be maintained after release.

As shown in Table 13, as with mannose gelator (M3), the results obtained reveal that the gels prepared by using glucose gelator (G4) can also be released.

Example 12

Spray Test

As shown in the results in Example 11, the gel prepared from the gelator of the present invention is a gel having solidity sufficient for self-standing, but is very fragile against shear to exhibit liquidity, and solidifies immediately after the shearing. Owing to these features, the gel of the present invention should be uniformly sprayed when used with an atomizer such as a sprayer typically used for cosmetics, and should immediately form a gel after spray, thus achieving good coating characteristics without dripping, The spray test was carried out as follows. Into a sample tube, glucose gelator (G3 or G6) and a mixed solvent of water and ethanol (75/25 or 50/50 (vol/vol) (4 mL) were added so as to give a concentration of 0.25 wt %, and the mixture was heated at 80° C. for 30 minutes and dissolved. The solution was then poured into a spray vial (manufactured by Maruemu Corporation, No. 3L) and allowed to cool to room temperature for 1 hour, yielding a gel in the spray vial. Next, the gel in the spray vial prepared was sprayed toward a glass plate (10×7.5 cm) positioned 4 cm apart from the spray vial, and whether the gel can be sprayed was evaluated. The expanse (height and width) of the sprayed gel and dripping after 1 minute were observed. The spray test results are shown in Table 14.

TABLE 14

Spray test results

| Gelator | G3 | G6 |
|---|---|---|
| Gelator concentration | 0.25 wt % | |
| Water/ethanol (v/v) | 75/25 | 50/50 |
| Spray | Possible | Possible |
| Height/cm | 2.0 | 2.9 |
| Width/cm | 2.2 | 3.2 |
| Dripping | None | None |

As shown in Table 14, the results obtained reveal that each of the gels prepared by using G3 and G6 was uniformly dispersed on the glass plate without dripping, and thus the gel can be sprayed. The results indicate that the gels prepared with G3 and G6 have thixotropic properties, as shown in Example 6. The gel can maintain the shape even when placed in reverse, and this suggests that the spray performance can be exerted even when a spray container is placed in reverse.

Example 13

Sol-Gel Phase Transition Temperature

Figure 10:
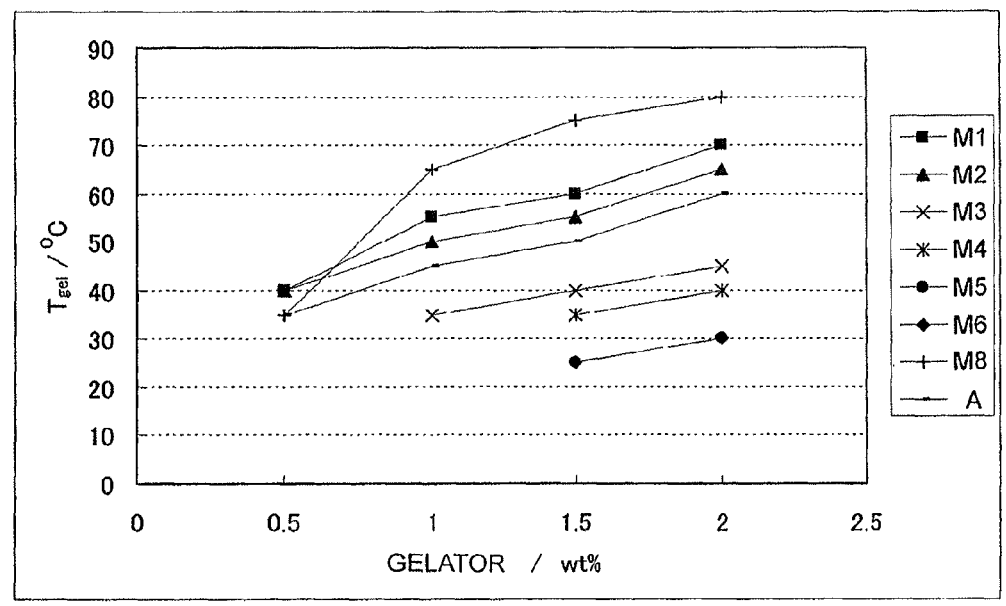
FIG. 10 is a view showing sol-gel phase transition temperature ($T_{gel}$) with respect to concentration of gelators in toluene gels prepared with mannose gelators M1 to M6 and M8 and compound A as a known substance.

A sol-gel phase transition temperature ($T_{gel}$) of a toluene gel was determined. For the measurement, a gel was prepared in a sample tube from toluene with mannose gelator (M1 to M6, M8) or compound A as a known substance. The sample tube was placed in an air bath the temperature of which was controlled, and left at 25° C. for 5 minutes. The sample tube was then taken out of the air bath and placed in reverse. Whether the gel was turned into a solution to fall down was observed. When a gel maintained the gel state, the air bath was adjusted to 30° C., then the sample tube containing the gel was placed in the air bath and left for 5 minutes, and the same operation was carried out. The operation was repeated while the temperature of the air bath was raised by 5° C., and the temperature at which the gel was turned into a solution to fall down when the sample tube placed in reverse was regarded as $T_{gel}$. FIG. 10 shows the sol-gel phase transition temperature ($T_{gel}$) with respect to the gelator concentration of the toluene gel prepared with each gelator.

A similar test was carried out by changing the solvent to SH245, and the gelator concentration of the SH245 gel prepared at a minimum gelation concentration and the sol-gel phase transition temperature ($T_{gel}$) are shown in Table 15.

TABLE 15

Sol-gel phase transition temperature of SH245 gel

|  | A | M1 | M2 | M3 | M4 | M5 | M6 | M8 | M10 |
|---|---|---|---|---|---|---|---|---|---|
| Concentration/wt % | 0.025 | 0.05 | 0.05 | 0.05 | 0.25 | 0.25 | 0.5 | 0.05 | 0.1 |
| $T_{gel}$/° C. | 55 | 85 | 70 | 70 | 95 | 95 | 100 | 90 | 40 |

As shown in FIG. 10, the results obtained reveal that each toluene gel has a tendency to have a higher sol-gel phase transition temperature $T_{gel}$ as the gelator concentration increases, and each toluene gel has a lower sol-gel phase transition temperature as the gelator has a longer alkyl chain as the hydrocarbon group bonded to the benzene ring. This is supposed to be because the gelator itself obtains higher affinity with the solvent. The comparison of gelators M2 (CH$_3$(CH$_2$)$_3$O—) and M8 (3-butenyl-O—) both of which had alkyl chains having the same length reveals that the sol-gel phase transition temperature is increased by introducing an olefinic structure to an alkyl end.

As shown in Table 15, the results obtained reveal that the SH245 gels prepared by using gelators M1 to M6 and M8 had higher sol-gel phase transition temperatures as compared with known gelator compound A as a known substance. This indicates that the gelator of the present invention can form a thermally stable gel as compared with known compound A.

Example 14

SEM Observation of Toluene Gel (Xerogel)

A toluene gel containing 1 wt % of mannose gelator M2 prepared in Example 1 or compound A as a known substance was prepared, and the gel was dried under vacuum for 24 hours to yield a xerogel, which was observed under a scanning microscope (SEM). The obtained results are shown in FIG. 11.

Figure 11:
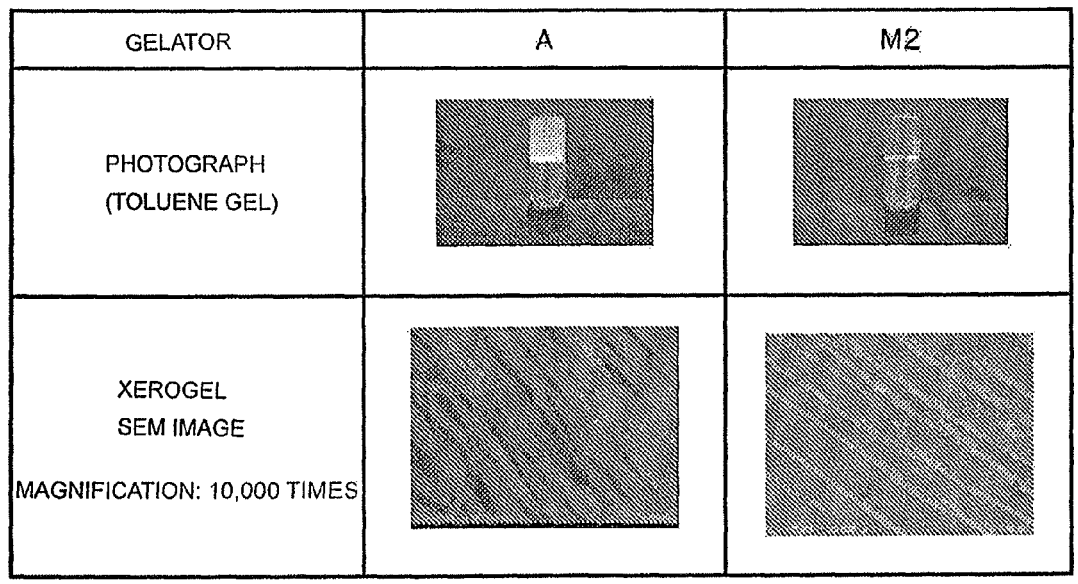
FIG. 11 is a view showing the appearances of toluene gels (1 wt %) prepared with mannose gelator M2 and compound A as a known substance and SEM images of xerogels thereof.

From the SEM images shown in FIG. 11, the image of the toluene gel (xerogel) with gelator A shows fibers having a width of about 500 nm to 800 nm, and the image of the toluene gel (xerogel) with gelator M2 shows plates.

Example 15

AFM Observation of Toluene Gel (Xerogel) with Gelator M2 or M6

In order to obtain detailed information of the plates of the toluene gel (xerogel) that are observed in the SEM image in Example 14 and obtained with the gelator of the present invention, AFM image observation was carried out.

Figure 12:
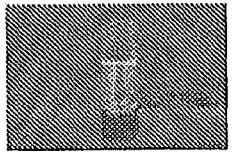
FIG. 12 is a view showing the appearances of toluene gels prepared with mannose gelators M2 and M6 and AFM images of xerogels thereof.
Figure 12:
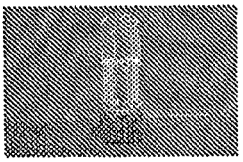
Figure 12:
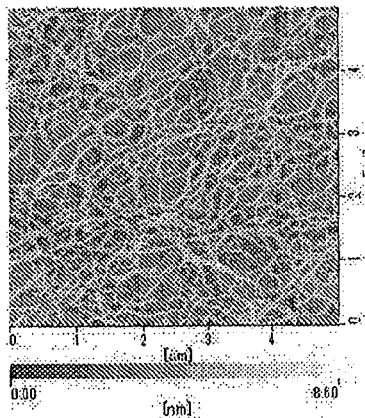
Figure 12:
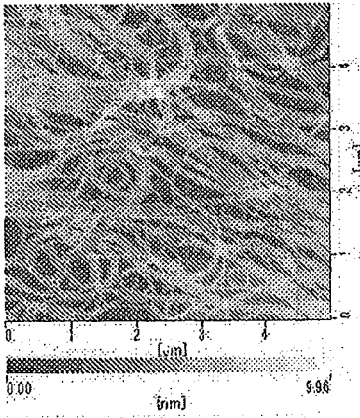

A toluene solution containing mannose gelator M2 (0.02 wt %) or M6 (0.02 wt %) synthesized in Example 1 was heated at 100° C., and the solution was cast on a graphite substrate (HOPG). The solution on HOPG was left for 1 hour and dried under vacuum for 24 hours, and the HOPG was observed under an atomic force microscope (AFM). The obtained results are shown in FIG. 12. FIG. 12 also shows photographs of the appearances of gels formed at minimum gelation concentrations (M2: 0.5 wt %, M6: 2 wt %).

From the AFM images shown in FIG. 12, the gel (xerogel) prepared from the toluene solution containing gelator M2 had a fiber structure having a height of about 3.5 nm from the HOPG. The result suggests that the plate of gelator M2 observed in the SEM image in Example 13 seems to be formed by bundling fiber structures having a width of about 3.5 nm.

By comparing the gels (xerogels) prepared from respective toluene solutions containing gelators M2 and M6 under AFM, the obtained result reveal that the gel (xerogel) prepared from the toluene solution containing M2 seems to form a fiber structure having a height of about 3.5 nm, and the gel (xerogel) prepared from the toluene solution containing M6 seems to form a tape-like structure by bundling fibers having a height of 3.1 nm to 3.8 nm.

Example 16

SEMM Observation of Toluene Gel and Aqueous Gel (Xerogels) Using Gelator M2

A toluene gel was prepared by using 0.5 wt % of mannose gelator M2 produced in Example 1. An aqueous gel was prepared by using 0.1 wt % of mannose gelator M2. Each gel was freeze-dried for 24 hours, and the obtained xerogel was observed under SEM. The obtained results are shown in FIG. 13.

Figure 13:
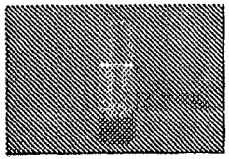
FIG. 13 is a view showing the appearances of a toluene gel (0.5 wt %) and an aqueous gel (0.1 wt %) prepared with mannose gelator M2 and SEM images of xerogels thereof.
Figure 13:
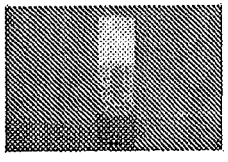
Figure 13:
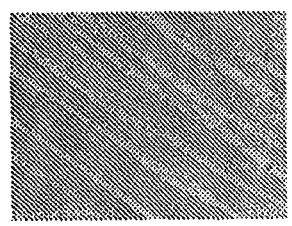
Figure 13:
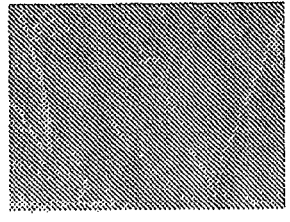

From the SEM images shown in FIG. 13, the results obtained reveal that the toluene gel (xerogel) is a plate formed by bundling fibers, and the aqueous gel (xerogel) forms a fiber structure having a width of about 200 nm.

Example 17

SEM Observation of Aqueous Gel (Xerogel)

An aqueous gel was prepared by using 0.1 wt % of mannose gelator M2 or glucose gelator G3 produced in Example 1 and was freeze-dried for 24 hours to yield a xerogel, which was observed under SEM. The obtained results are shown in FIG. 14.

Figure 14:
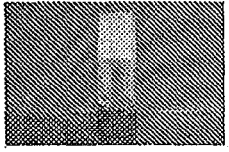
FIG. 14 is a view showing the appearances of aqueous gels (0.1 wt %) prepared with mannose gelator M2 and glucose gelator G3 and SEM images of xerogels thereof.
Figure 14:
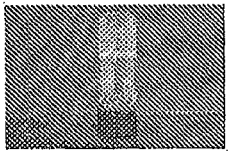
Figure 14:
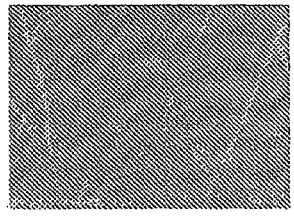
Figure 14:
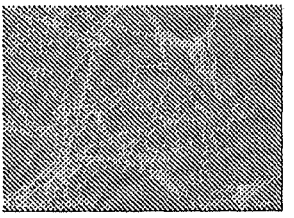

From the SEM images shown in FIG. 14, the results obtained reveal that the aqueous gel (xerogel) formed by using M2 forms a fiber structure having a width of about 200 nm, and the aqueous gel (xerogel) formed by using G3 forms a fiber structure having a width of about 40 to 50 nm.

The results obtained above reveal that by changing the sugar structure of the gelator from mannose to glucose, the aqueous gel obtains high transparency, and the fiber structure formed of each gelator tends to have a smaller width.

The invention claimed is:

1. A gelator comprising:
a compound of Formula (1) or Formula (2):

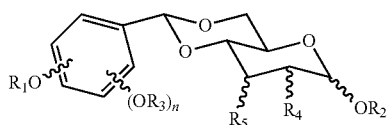
(1)

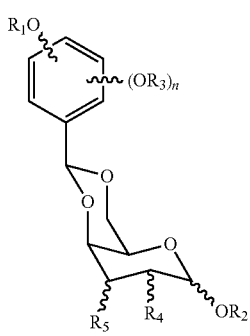
(2)

(where
each of $R_1$ and $R_3$ is independently a linear or branched alkyl group having a carbon atom number of 1 to 20, a cyclic $C_{3-20}$ alkyl group, or a linear or branched alkenyl group having a carbon atom number of 2 to 20; n is 0 or an integer of 1 to 4;
$R_2$ is a hydrogen atom, a linear or branched alkyl group having a carbon atom number of 1 to 10, or an aryl group optionally having a substituent; and
$R_4$ and $R_5$ are each a hydroxy group).

2. The gelator according to claim 1, wherein the compound of Formula (1) is a compound of Formula (3):

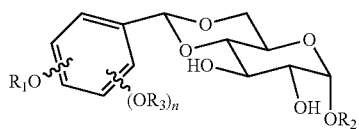
(3)

[where $R_1$, $R_2$, $R_3$, and n are the same as the respective definitions described in Formula (1)].

3. The gelator according to claim 1, wherein the compound of Formula (1) is a compound of Formula (4):

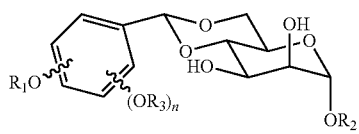
(4)

[where $R_1$, $R_2$, $R_3$, and n are the same as the respective definitions described in Formula (1)].

4. A gel comprising:
the gelator as claimed in claim 1; and
a hydrophobic organic solvent, a hydrophilic organic solvent, water, a hydrophilic organic solution, a hydrophobic organic solution, or an aqueous solution.

5. The gel according to claim 4, wherein the hydrophobic organic solvent is at least one selected from the group consisting of plant oils, esters, silicone oils, and hydrocarbons.

6. The gel according to claim 4, wherein the hydrophilic organic solvent is at least one selected from the group consisting of methanol, ethanol, 2-propanol, i-butanol, pentanol, hexanol, 1-octanol, isooctanol, acetone, cyclohexanone, acetonitrile, dioxane, glycerol, propylene glycol, ethylene glycol, and dimethyl sulfoxide.

7. The gel according to claim 4, wherein the hydrophilic organic solution is a mixed solvent of the hydrophilic organic solvent selected from the group consisting of methanol, ethanol, 2-propanol, i-butanol, pentanol, hexanol, 1-octanol, isooctanol, acetone, cyclohexanone, acetonitrile, dioxane, glycerol, propylene glycol, ethylene glycol, and dimethyl sulfoxide and water.

8. The gel according to claim 4, wherein the hydrophobic organic solution is a mixed solvent of the hydrophobic organic solvent selected from the group consisting of plant oils, esters, silicone oils, and hydrocarbons and water.

9. The gel according to claim 4, wherein the aqueous solution is an aqueous solution containing an organic acid, an inorganic acid, at least one inorganic salt selected from the group consisting of inorganic carbonates, inorganic sulfates, inorganic phosphates, and inorganic hydrogen phosphates, or at least one organic salt selected from the group consisting of acetates, lactates, citrates, organic amine hydrochlorides, and organic amine acetates.

10. The gel according to claim 9, wherein the organic acid is at least one selected from the group consisting of acetic acid, citric acid, succinic acid, lactic acid, malic acid, maleic acid, fumaric acid, and trifluoroacetic acid, the inorganic acid is at least one selected from the group consisting of hydrochloric acid, phosphoric acid, carbonic acid, sulfuric acid, nitric acid, and boric acid, the inorganic salt is at least one selected from the group consisting of calcium carbonate, sodium carbonate, potassium carbonate, sodium sulfate, potassium sulfate, magnesium sulfate, potassium phosphate, sodium phosphate, disodium hydrogen phosphate, and sodium dihydrogen phosphate, and the organic salt is at least one selected from the group consisting of sodium acetate, potassium acetate, sodium lactate, potassium lactate, sodium citrate, potassium citrate, ethylenediamine hydrochloride, ethylenediaminetetraacetate, and trishydroxymethylaminomethane hydrochloride.

11. A base material for cosmetics or a base material for medical use, the base material comprising:
the gelator as claimed in claim 1.

12. A base material for cosmetics or a base material for medical use, the base material comprising:
the gelator as claimed in claim 1; and
at least one polymer compound.

13. A gel electrolyte comprising:
the gelator as claimed in claim 1.

14. A cell culture base material comprising:
the gelator as claimed in claim 1.

15. A base material for preserving biomolecules, the base material comprising:
the gelator as claimed in claim 1.

16. A base material for external use, the base material comprising:
the gelator as claimed in claim 1.

17. A base material for biochemistry, the base material comprising:
the gelator as claimed in claim 1.

18. A base material for food, the base material comprising:
the gelator as claimed in claim 1.

19. A base material for dryland farming, the base material comprising:
the gelator as claimed in claim 1.

20. A method for producing the compound of Formula (1) or Formula (2) as claimed in claim 1, the method comprising:
reacting a compound of Formula [A]:

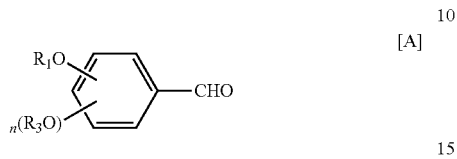

(where each of $R_1$ and $R_3$ is independently a linear or branched alkyl group having a carbon atom number of 1 to 20, a cyclic $C_{3-20}$ alkyl group, or a linear or branched alkenyl group having a carbon atom number of 2 to 20; and n is 0 or an integer of 1 to 4) with an acetalizing agent, and subsequently subjecting the obtained acetal derivative to annulation reaction with glucose, mannose, a derivative of glucose, or a derivative of mannose, thus producing the compound of Formula (1) or Formula (2), wherein
the reactions are carried out in a one-pot system in the presence of ethanol and p-toluenesulfonic acid.

\* \* \* \* \*